(12) United States Patent
Murdock et al.

(10) Patent No.: US 6,479,074 B2
(45) Date of Patent: *Nov. 12, 2002

(54) METHODS AND TRANSDERMAL COMPOSITIONS FOR PAIN RELIEF

(75) Inventors: Robert W. Murdock, Selah, WA (US); C. Donald Williams, Yakima, WA (US)

(73) Assignee: Pharmaceutical Applications Associates LLC, Yakima, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/825,375

(22) Filed: Apr. 2, 2001

(65) Prior Publication Data

US 2002/0009487 A1 Jan. 24, 2002

Related U.S. Application Data

(60) Division of application No. 09/652,662, filed on Aug. 31, 2000, and a division of application No. 09/342,679, filed on Jun. 29, 1999, now abandoned, and a continuation-in-part of application No. 09/106,684, filed on Jun. 29, 1998, now Pat. No. 6,290,986, which is a continuation-in-part of application No. PCT/US97/19651, filed on Oct. 24, 1997, and a continuation-in-part of application No. 08/957,485, filed on Oct. 24, 1997, now abandoned.

(60) Provisional application No. 60/122,903, filed on Mar. 5, 1999, and provisional application No. 60/029,120, filed on Oct. 24, 1996.

(51) Int. Cl.[7] .............................................. A61F 13/00
(52) U.S. Cl. ...................... 424/449; 424/447; 424/448; 424/484; 514/78; 514/906
(58) Field of Search ............................... 424/447, 448, 424/449, 484; 514/906, 78

(56) References Cited

U.S. PATENT DOCUMENTS 4,221,788 A  9/1980  Eistetter .................. 424/244
4,370,324 A  1/1983  Bernstein .................. 424/244

(List continued on next page.)

FOREIGN PATENT DOCUMENTS

| WO | WO 8900077 | 1/1989 |
| WO | WO 9301812 | 2/1993 |
| WO | WO 9528152 | 10/1995 |

OTHER PUBLICATIONS

Cohn, M. J. et al., "Proxicam and Doxepin—An Alternative to Narcotic Analgesics in managing Advanced Cancer Pain," *The Western Journal of Medicine*, vol. 148(3), pp. 303–306 (Mar. 1988).

"Doxepin Cream for Pruritus," *The Medical Letter on Drugs and Therapeutics*, vol. 36 (Issue 934), pp. 933–938 (Oct. 28, 1994).

Godfrey, Robert G., "A Guide to the Understanding and Use of Tricyclic Antidepressants in the Overall Management of Fibromyalgia and Other Chronic Pain Syndromes," *Arch. Intern. Med.*, vol. 156, pp. 1047–1052.

Iacono, R. P. et al., "Post–Amputation Phantom Pain and Autonomous Stump Movements Responsive to Doxepin," *Funct. Neurol.*, vol. 2(3), pp. 343–348 (1987).

Pelton, James, "Piroxicam and Doxepin in Pain Management," *The Western Journal of Medicine*, vol. 194(1), p. 93 (Jul. 1988).

(List continued on next page.)

*Primary Examiner*—Thurman K. Page
*Assistant Examiner*—Lakshmi S. Channavajjala
(74) *Attorney, Agent, or Firm*—Lahive & Cockfield LLP; Giulio A. DeConti; Maria C. Laccotripe

(57) ABSTRACT

The present invention features methods and compositions for transdermal administration. In one embodiment, the invention features methods and compositions for transdermal administration of an amine containing compound having biphasic solubility and/or an agent which enhances the activity of the amine containing compound having biphasic solubility, e.g., a muscle relaxant, to relieve pain.

17 Claims, 11 Drawing Sheets

U.S. PATENT DOCUMENTS

| | | | |
|---|---|---|---|
| 4,395,420 A | 7/1983 | Bernstein | 424/278 |
| 4,603,131 A | 7/1986 | Bernstein et al. | 514/220 |
| 4,668,232 A | 5/1987 | Cordes et al. | 604/897 |
| 4,788,063 A | 11/1988 | Fisher et al. | 424/449 |
| 4,794,000 A | 12/1988 | Ecanow | 424/457 |
| 4,876,260 A | 10/1989 | Fisher et al. | 514/278 |
| 4,914,084 A | 4/1990 | Ecanow | 514/6 |
| 4,963,367 A | 10/1990 | Ecanow | 424/485 |
| 4,981,858 A | 1/1991 | Fisher et al. | 514/278 |
| 5,008,289 A | 4/1991 | Bernstein | 414/535 |
| 5,106,831 A | 4/1992 | Fisher et al. | 514/2 |
| 5,164,398 A | 11/1992 | Sims et al. | 514/282 |
| 5,292,499 A | 3/1994 | Evans et al. | 424/45 |
| 5,326,570 A | 7/1994 | Rudnic et al. | 424/458 |
| 5,356,934 A | 10/1994 | Robertson et al. | 514/649 |
| 5,446,070 A | 8/1995 | Mantelle | 514/772.6 |
| 5,478,828 A | 12/1995 | Mattson et al. | 514/253 |
| 5,538,993 A | 7/1996 | Mechoulam et al. | 514/454 |
| 5,560,910 A | 10/1996 | Crandall | 424/94.63 |
| 5,601,839 A | 2/1997 | Quan et al. | 424/448 |
| 5,639,740 A | 6/1997 | Crandall | 514/78 |
| 5,654,337 A | 8/1997 | Roentsch et al. | 514/570 |
| 5,656,286 A | 8/1997 | Miranda et al. | 424/449 |
| 5,693,337 A | 12/1997 | Suzuki et al. | 424/450 |
| 5,708,035 A | 1/1998 | Young et al. | 514/649 |
| 5,837,289 A | 11/1998 | Grasela et al. | 424/484 |
| 5,885,597 A | 3/1999 | Botknecht et al. | 424/401 |
| 5,891,472 A | 4/1999 | Russell | 424/484 |
| 5,900,249 A | 5/1999 | Smith | 424/443 |
| 5,922,341 A | 7/1999 | Smith et al. | 424/430 |
| 5,945,409 A | 8/1999 | Crandall | 514/78 |
| 5,948,777 A | 9/1999 | Bender et al. | 514/235.8 |
| 5,976,547 A | 11/1999 | Archer et al. | 424/195.1 |
| 6,045,827 A | 4/2000 | Russell | 424/485 |

OTHER PUBLICATIONS

Pettengill, C.A. et al., "The Use of Tricyclic Antidepressants for the Control of Chronic Orofacial Pain," *The Journal of Craniomandibular Practice,* vol. 15(1), pp. 53–56 (Jan. 1997).

Richeimer, S. H. et al., "Utilization Patterns of Tricyclic Antidepressants in a Multidisciplinary Pain Clinic: A Survey," *The Clinical Journal of Pain,* vol. 13, pp. 324–349 (1997).

cpt 90862 Medication Management (cdw ver. 4-24-95)                                    90862.DOC Patient: _____ Date _____

Current Medication:   1) _____
                             2) _____
                             3) _____
                             4) _____
                             5) _____
                             6) _____

Diagnoses:   Axis 1: _____
                            _____   Axis 3: _____
             Axis 2: _____   GAF _____

Subjective: _____
_____
_____
_____
_____
_____

Objective :   APPEARANCE _____        AFFECT _____
               SPEECH _____        CONCENTRATION _____
               MEMORY _____        IRRITABILITY _____
               APPETITE _____       A/V HALLUC. _____
               CRYING SPELLS _____        ENERGY LEVEL _____
               SLEEP _____        WEIGHT _____
SIDE EFFECTS: _____

RESPONSE OF DEPRESSION SYMPTOMS TO MEDICATIONS:
       EXCELLENT            GOOD            FAIR            POOR            N/A

RESPONSE OF ANXIETY SYMPTOMS TO MEDICATIONS:
       EXCELLENT            GOOD            FAIR            POOR            N/A

CONCURRENT MEDICATION CONDITIONS: _____
_____

ASSESSMENT: _____
_____
_____
_____

PLAN:   1) Continue meds: _____
           2) Change dosage: _____
           3) New Med: _____
           4) _____

LAB STUDIES ORDERED: _____
OTHER: _____

Fig. 1

Case Processing Summary(a)

| | Cases | | | | | |
|---|---|---|---|---|---|---|
| | Included | | Excluded | | Total | |
| | N | Percent | N | Percent | N | Percent |
| ankle * MEDS * Composition | 4 | 3.1% | 127 | 96.9% | 131 | 100.0% |
| arm * MEDS * Composition | 10 | 7.6% | 121 | 92.4% | 131 | 100.0% |
| Back * MEDS * Composition | 69 | 52.7% | 62 | 47.3% | 131 | 100.0% |
| elbow * MEDS * Composition | 11 | 8.4% | 120 | 91.6% | 131 | 100.0% |
| headache * MEDS * Composition | 131 | 100.0% | 0 | .0% | 131 | 100.0% |
| Knee * MEDS * Composition | 19 | 14.5% | 112 | 85.5% | 131 | 100.0% |
| hip * MEDS * Composition | 15 | 11.5% | 116 | 88.5% | 131 | 100.0% |
| Neck * MEDS * Composition | 28 | 21.4% | 103 | 78.6% | 131 | 100.0% |
| leg * MEDS * Composition | 13 | 9.9% | 118 | 90.1% | 131 | 100.0% |
| shoulder * MEDS * Composition | 25 | 19.1% | 106 | 80.9% | 131 | 100.0% |
| wrist * MEDS * Composition | 26 | 19.8% | 105 | 80.2% | 131 | 100.0% |
| a Limited to first 150 cases | | | | | | |

| | | | | | Case Number | ankle | arm |
|---|---|---|---|---|---|---|---|
| c-dox-gu | Composition | | 5/5/10 | 1 | 26 | . | . |
| | | | | 2 | 33 | . | . |
| | | | | 3 | 41 | . | . |
| | | | | 4 | 59 | . | . |
| | | | | 5 | 73 | . | . |
| | | | | 6 | 80 | . | . |
| | | | Total | N | | | |
| | | | | Mean | | | |
| | | | 4/5/10 | 1 | 98 | . | . |
| | | | | 2 | 112 | . | . |
| | | | Total | N | | | |
| | | | | Mean | | | |

Fig. 2A

| | | | | | | | |
|---|---|---|---|---|---|---|---|
| c-gab-do | Composition | | Total | N | | | |
| | | | | Mean | | | |
| | | 5/5/5 | | 1 | 34 | . | . |
| | | | Total | N | | | |
| | | | | Mean | | | |
| | | Total | | N | | | |
| | | | | Mean | | | |
| carb | Composition | 4 | | 1 | 5 | . | . |
| | | | Total | N | | | |
| | | | | Mean | | | |
| | | 6 | | 1 | 81 | . | . |
| | | | Total | N | | | |
| | | | | Mean | | | |
| | | Total | | N | | | |
| | | | | Mean | | | |
| carb-ami | Composition | 4/5 | | 1 | 12 | . | . |
| | | | | 2 | 40 | . | . |
| | | | | 3 | 49 | . | . |
| | | | | 4 | 64 | . | . |
| | | | Total | N | | | |
| | | | | Mean | | | |
| | | Total | | N | | | |
| | | | | Mean | | | |
| carb-gab | Composition | 4/4 | | 1 | 27 | . | mild-moderate |
| | | | | 2 | 35 | . | . |
| | | | | 3 | 126 | . | moderate |
| | | | Total | N | | | 2 |
| | | | | Mean | | | 1.750 |
| | | Total | | N | | | 2 |
| | | | | Mean | | | 1.750 |
| | | | | 1 | 4 | . | moderate |
| | | | | 2 | 13 | . | . |
| | | | | 3 | 15 | . | . |

Fig. 2B

| | | | | | | |
|---|---|---|---|---|---|---|
| dox | Composition | 5 | 4 | 42 | . | . |
| | | | 5 | 46 | . | none |
| | | | 6 | 74 | . | . |
| | | | 7 | 95 | moderate | . |
| | | | 8 | 116 | . | . |
| | | | 9 | 121 | . | . |
| | | | 10 | 128 | . | moderate |
| | | | Total N | | 1 | 3 |
| | | | Mean | | 2.000 | 1.333 |
| | Total | N | | | 1 | 3 |
| | | Mean | | | 2.000 | 1.333 |
| dox-chl | Composition | 7/13 | 1 | 10 | . | . |
| | | | Total N | | | |
| | | | Mean | | | |
| | | 5/10 | 1 | 21 | . | . |
| | | | 2 | 29 | . | . |
| | | | 3 | 30 | . | . |
| | | | Total N | | | |
| | | | Mean | | | |
| | | 7/10 | 1 | 83 | . | . |
| | | | Total N | | | |
| | | | Mean | | | |
| | Total | N | | | | |
| | | Mean | | | | |
| | | | 1 | 7 | . | . |
| | | | 2 | 9 | . | . |
| | | | 3 | 14 | . | . |
| | | | 4 | 18 | . | . |
| | | | 5 | 20 | . | . |
| | | | 6 | 25 | . | . |
| | | | 7 | 36 | . | . |
| | | | 8 | 50 | . | . |

Fig. 2C

| | | | | | | | |
|---|---|---|---|---|---|---|---|
| dox-guai | Compsition | 5/10 | 9 | 58 | . | | . |
| | | | 10 | 71 | . | | . |
| | | | 11 | 76 | . | | . |
| | | | 12 | 77 | . | | . |
| | | | 13 | 90 | . | | . |
| | | | 14 | 97 | . | | . |
| | | | 15 | 101 | . | | . |
| | | | 16 | 103 | . | | . |
| | | | 17 | 108 | . | | . |
| | | | 18 | 123 | . | | . |
| | | | 19 | 131 | . | | . |
| | | | Total | N | | | |
| | | | | Mean | | | |
| | | 7/10 | 1 | 22 | . | | . |
| | | | 2 | 47 | . | | . |
| | | | 3 | 111 | . | | . |
| | | | Total | N | | | |
| | | | | Mean | | | |
| | | 10/10 | 1 | 23 | . | | . |
| | | | 2 | 48 | . | | . |
| | | | 3 | 53 | . | | . |
| | | | 4 | 57 | . | | . |
| | | | 5 | 67 | . | | . |
| | | | Total | N | | | |
| | | | | Mean | | | |
| | | Total | N | | | | |
| | | | Mean | | | | |
| | | 4/5/10 | 1 | 11 | . | | . |
| | | | Total | N | | | |
| | | | | Mean | | | |
| | | | 1 | 1 | . | | . |
| | | | 2 | 32 | . | | . |
| | | | 3 | 39 | . | | . |

Fig. 2D

| MEDS | g-dox-gu | Composition | 5/5/10 | 4 | | 44 | . | . |
| | | | | 5 | | 51 | . | . |
| | | | | 6 | | 54 | . | . |
| | | | | 7 | | 62 | . | . |
| | | | | 8 | | 72 | . | . |
| | | | | 9 | | 85 | . | . |
| | | | | 10 | | 87 | . | . |
| | | | | 11 | | 93 | . | . |
| | | | | 12 | | 119 | . | . |
| | | | | 13 | | 129 | . | . |
| | | | | Total | N | | | |
| | | | | | Mean | | | |
| | | Total | | N | | | | |
| | | | | Mean | | | | |
| | gab-dox | Composition | 5/5 | 1 | | 37 | . | . |
| | | | | 2 | | 65 | . | . |
| | | | | 3 | | 68 | . | . |
| | | | | Total | N | | | |
| | | | | | Mean | | | |
| | | Total | | N | | | | |
| | | | | Mean | | | | |
| | k-ca-dox | Composition | 10/4/5 | 1 | | 86 | . | . |
| | | | | Total | N | | | |
| | | | | | Mean | | | |
| | | Total | | N | | | | |
| | | | | Mean | | | | |
| | | | 10/6/3 | 1 | | 43 | . | . |
| | | | | Total | N | | | |
| | | | | | Mean | | | |
| | | | | 1 | | 102 | . | . |

Fig. 2E

| | | | | | | |
|---|---|---|---|---|---|---|
| k-car-pi | Composition | 10/4/3 | 2 | 104 | . | . |
| | | | Total | N | | |
| | | | | Mean | | |
| | | Total | N | | | |
| | | | Mean | | | |
| k-dox-ch | Composition | 20/10/5 | 1 | 100 | . | . |
| | | | Total | N | | |
| | | | | Mean | | |
| | | Total | N | | | |
| | | | Mean | | | |
| k-dox-gu | Composition | 3/5/5 | 1 | 6 | . | . |
| | | | Total | N | | |
| | | 20/5/10 | 1 | 63 | . | . |
| | | | Total | N | | |
| | | | | Mean | | |
| | | Total | N | | | |
| | | | Mean | | | |
| k-dox-pi | Composition | 10/4/3/5 | 1 | 122 | . | . |
| | | | Total | N | | |
| | | | | Mean | | |
| | | Total | N | | | |
| | | | Mean | | | |
| k-g-do-g | Composition | 10/4/5/10 | 1 | 17 | . | . |
| | | | Total | N | | |
| | | | | Mean | | |
| | | Total | N | | | |
| | | | Mean | | | |
| k-gab | Composition | 20/4 | 1 | 115 | none | |
| | | | Total | N | . | 1 |
| | | | | Mean | | .000 |
| | | Total | N | | | 1 |
| | | | Mean | | | .000 |
| | | | 1 | 117 | . | . |

Fig. 2F

| | | | | | | | |
|---|---|---|---|---|---|---|---|
| k-gab-am | Composition | 20/5/5 | Total | N | | | |
| | | | | Mean | | . | . |
| | | Total | | N | | | |
| | | | | Mean | | | |
| k-gab-do | Composition | 20/4/5 | | 1 | 55 | . | . |
| | | | Total | N | | | |
| | | | | Mean | | | |
| | | 10/5/4 | | 1 | 99 | major | . |
| | | | Total | N | | 1 | |
| | | | | Mean | | 3.000 | |
| | | 10/5/5 | | 1 | 113 | . | . |
| | | | Total | N | | | |
| | | | | Mean | | | |
| | | 20/5/5 | | 1 | 118 | . | . |
| | | | Total | N | | | |
| | | | | Mean | | | |
| | | Total | | N | | 1 | |
| | | | | Mean | | 3.000 | |
| k-gab-gu | Composition | 20/4/4/1 | | 1 | 94 | . | . |
| | | | Total | N | | | |
| | | | | Mean | | | |
| | | 20/5/5 | | 1 | 105 | . | . |
| | | | Total | N | | | |
| | | | | Mean | | | |
| | | Total | | N | | | |
| | | | | Mean | | | |
| | | | | 1 | 2 | . | . |
| | | | | 2 | 8 | . | major |
| | | | | 3 | 19 | . | . |
| | | | | 4 | 31 | . | . |
| | | | | 5 | 38 | . | . |
| | | | | 6 | 45 | . | none |

Fig. 2G

| | | | | | | |
|---|---|---|---|---|---|---|
| | | | 10/4/3 | 7 | 56 | . | . |
| | | | | 8 | 78 | . | . |
| | | | | 9 | 89 | . | . |
| | | | | 10 | 109 | . | . |
| | | | | 11 | 120 | . | . |
| | | | | 12 | 124 | . | . |
| | | | | 13 | 130 | . | . |
| | | | Total | N | | | 2 |
| | | | | Mean | | | 1.500 |
| k-gab-pi | Composition | | | 1 | 16 | . | . |
| | | | | 2 | 28 | . | mild |
| | | | | 3 | 52 | . | . |
| | | | | 4 | 66 | . | . |
| | | | | 5 | 69 | . | . |
| | | | | 6 | 75 | moderate | . |
| | | | 10/4/1 | 7 | 82 | . | . |
| | | | | 8 | 84 | . | . |
| | | | | 9 | 88 | . | . |
| | | | | 10 | 91 | . | . |
| | | | | 11 | 96 | major | . |
| | | | | 12 | 125 | . | . |
| | | | Total | N | | 2 | 1 |
| | | | | Mean | | 2.500 | 1.000 |
| | | | 10/1/3 | 1 | 114 | . | . |
| | | | Total | N | | | |
| | | | Total | N | | 2 | 3 |
| | | | | Mean | | 2.500 | 1.333 |
| k-pi | Composition | | 10/3 | 1 | 127 | . | . |
| | | | | Total | N | | |
| | | | | | Mean | | |
| | | | Total | N | | | |
| | | | | Mean | | | |
| | | | | 1 | 110 | . | . |

Fig. 2H

| | | | | | | | |
|---|---|---|---|---|---|---|---|
| la-li-gu | Composition | 5/5/10 | Total | N | | | |
| | | | | Mean | | | |
| | | Total | | N | | | |
| | | | | Mean | | | |
| lam-chl | Composition | 7/10 | 1 | | 3 | . | moderate-major |
| | | | Total | N | | | 1 |
| | | | | Mean | | | 2.500 |
| | | 10/10 | 1 | | 24 | . | . |
| | | | 2 | | 70 | . | . |
| | | | 3 | | 106 | . | . |
| | | | Total | N | | | |
| | | | | Mean | | | |
| | | Total | | N | | | 1 |
| | | | | Mean | | | 2.500 |
| n-dox-ch | Composition | 30/5/5 | 1 | | 79 | . | . |
| | | | Total | N | | | |
| | | | | Mean | | | |
| | | Total | | N | | | |
| | | | | Mean | | | |
| naproxen | Composition | 30 | 1 | | 60 | . | . |
| | | | Total | N | | | |
| | | Total | | N | | | |
| tri-chl | Composition | 7/10 | 1 | | 61 | . | . |
| | | | Total | N | | | |
| | | | | Mean | | | |
| | | 7/13 | 1 | | 92 | . | . |
| | | | 2 | | 107 | . | . |
| | | | Total | N | | | |
| | | | | Mean | | | |
| | | Total | | N | | | |
| | | | | Mean | | | |

Fig. 21

|  | Total | N |  | 4 | 10 |
|---|---|---|---|---|---|
|  |  | Mean |  | 2.500 | 1.400 |
| June 2 1999 N=131 |||||||
| a Limited to first 150 cases |||||||

METHODS AND TRANSDERMAL COMPOSITIONS FOR PAIN RELIEF

CROSS-REFERENCE TO RELATED APPLICATIONS

This application claims priority to divisional application Ser. No. 09/652,662 filed Aug. 31, 2000, U.S. Pat. application No. 09/342,679 filed on Jun. 29, 1999, abandoned U.S. Provisional Patent Application No. 60/122,903 filed on Mar. 5, 1999, and is also a continuation-in-part of U.S. patent application Ser. No. 09/106,684 filed on Jun. 29, 1998, now U.S. Pat. No. 6,290,986 which is a continuation-in-part of PCT Application Ser. No. PCT/US97/19651 filed on Oct. 24, 1997, and a continuation-in-part of U.S. patent application Ser. No. 08/957,485 filed on Oct. 24, 1997, now abandoned, and U.S. Provisional Patent Application Ser. No. 60/029,120 filed on Oct. 24, 1996. The contents of all of the aforementioned application(s) are hereby incorporated by reference.

FIELD OF THE INVENTION

The present invention is directed to methods and compositions for transdermal administration. In particular, the present invention is directed to methods and compositions for the transdermal administration of an amine containing compound having biphasic solubility and/or an agent which enhances the activity of the amine containing compound having biphasic solubility, e.g., a muscle relaxant, to relieve pain.

BACKGROUND OF THE INVENTION

It is believed that damage to somatic sensory nerves causes a somatic sensory loss. Such damage can be caused by a variety of means including trauma, diseases such as diabetes, herpes zoster and late-stage cancer, chemotherapy, or by a chemical injury. It is believed that neural pain circuits rewire themselves, both anatomically and biochemically, after nerve injury. In many patients suffering from damage to somatic sensory nerves, negative symptoms such as numbness are joined by positive sensations, involving a sort of false sensation of pain. The experience can range from mild dysesthesia to excruciating pain, rendering some patients unable to work, walk or do other daily activities.

In the past, patients were generally treated by administration of analgesics to relieve pain. A vast majority of such patients receive doses of these agents orally. Unfortunately, in some situations, oral administration of such agents has been associated with a variety of side effects, such as liver damage, kidney damage, gastrointestinal side effects, addiction, sedation, and/or weight gain which cannot be tolerated well by the patient. In other cases, malabsorption of oral preparations have resulted in subtherapeutic plasma levels. In other cases, the agents have relatively short plasma half-lives, necessitating inconveniently frequent dosing. In general, oral delivery involves a time delay as the analgesic is absorbed via the digestive system before entering the bloodstream. A number of agents which have traditionally been administered orally or by injection have been inappropriate or suboptimal for some patients when so-administered. There are a number of medications which, in at least some patients, are not tolerated well when orally administered (e.g. which cause undesirable gastrointestinal or other side effects) and/or which provide undesirably high or low concentrations or delayed concentrations in a target tissue. In some cases, dosages which are appropriate for oral administration, upon being distributed more or less uniformly throughout the body, are undesirably low in a particular area, e.g., tissue, to achieve desired results. Oral or injection administration may result in too slow or too rapid increase in blood plasma levels, e.g., may involve an undesirably long time delay as the analgesic is absorbed by the digestive system before entering the bloodstream, or may result in a "spike" in blood plasma levels followed by an undesirably low level, where a more constant level would be preferable. Some analgesics are particularly prone to cause or contribute to kidney or liver damage when administered orally.

Although other forms of delivery of pharmaceuticals agents are known, each has its drawbacks. Parenteral (i.e., intravenously or intramuscularly injected) administration is inconvenient and expensive, and is rarely used outside the hospital. Inhalation is believed to be not feasible with many analgesic agents currently in use. Therefore, there is a need for an analgesic delivery system which provides effective and acceptable levels, while preferably avoiding or reducing undesired effects such as liver damage or gastrointestinal side effects.

SUMMARY OF THE INVENTION

The present invention provides a transdermal composition for the treatment of pain in a subject, particularly a human subject. The transdermal composition for the treatment of pain in a subject includes an amine containing compound having biphasic solubility in an amount effective to treat pain in a subject and a pharmaceutically acceptable carrier suitable for transdermal delivery of the amine containing compound, e.g., a lecithin organogel carrier. In a preferred embodiment, the transdermal composition further includes an agent which enhances the activity of the amine containing compound having biphasic solubility, e.g., a muscle relaxant, such as guaifenesin, chlorzoxazone, dantrolene sodium, metaxalone, carisoprodol, and combinations thereof. Preferably, the agent which enhances the activity of the amine containing compound having biphasic solubility, e.g., the muscle relaxant, also has a biphasic solubility.

In one embodiment of the present invention, the amine containing compound having biphasic solubility is an anti-depressant compound, such as a tricyclic antidepressant compound, e.g., doxepin or trimipramine.

In another embodiment of the present invention, the amine containing compound having biphasic solubility is a sodium channel blocker, an anti-epileptic compound, or an anti-convulsant compound.

Another embodiment of the invention features a transdermal composition which includes an amine-containing compound as described herein and an anti-inflammatory compound, such as a nonsteroidal anti-inflammatory compound, e.g., celecoxib, etodolac, mefanamic acid, nabumetone, salsalate, naproxen, vioxx®, and combinations thereof. Such a composition can further include an agent which enhances the activity of the amine containing compound, e.g., a muscle relaxant such as guaifenesin.

In another aspect, the invention features a transdermal composition for the treatment of pain in a subject including an amine containing compound having biphasic solubility in an amount effective to treat pain in a subject; a muscle relaxant in an amount effective to enhance the activity of the amine containing compound having biphasic solubility; and a pharmaceutically acceptable carrier suitable for transdermal delivery of the amine containing compound having biphasic solubility and the muscle relaxant.

In yet another aspect, the invention features a transdermal composition for the treatment of pain in a subject including doxepin in an amount effective to treat pain in a subject-;.guaifenesin in an amount effective to enhance the activity of doxepin; and a pharmaceutically acceptable carrier suitable for transdermal delivery of the doxepin and the guaifenesin.

Other aspects of the invention feature methods for treating pain in a subject in which the subject is contacted with a transdermal composition including an amine containing compound having biphasic solubility in an amount effective to treat pain in the subject; and a pharmaceutically acceptable carrier suitable for transdermal delivery of the amine containing compound to thereby treat pain in the subject. In a preferred embodiment, the transdermal composition is applied to the skin of the subject.

Another aspect of the invention features a method for selecting a compound suitable for treating pain in a subject. The method includes transdermally administering an amine containing compound having biphasic solubility to a subject; and determining whether pain is treated in the subject to thereby select a compound suitable for treating pain in a subject. In a preferred embodiment, the method can further include modeling the compound using a computer equipped with a three-dimensional chemical structure modeling program; and determining whether the three dimensional chemical structure of the compound possesses sufficient characteristics to be useful as a sodium channel blocker, thereby selecting a compound suitable for treating pain in a subject.

In another aspect, the invention features a transdermal composition suitable for transdermal delivery, which includes a therapeutically effective amount of a pharmaceutical compound (e.g., a serotonin specific reuptake inhibitor, a mood stabilizing compound, a dopamine compound, a compound suitable for treating attention deficit hyperactivity disorder, a compound suitable for treating hypertension and akathisia, an analgesic compound, or a compound used in the treatment of impotence) and a pharmaceutically acceptable carrier suitable for transdermal delivery of the pharmaceutical compound, e.g., a lecithin organogel carrier.

In yet another aspect, the invention features a transdermal composition for treatment of pain in a subject which includes a compound capable of blocking afferent neuron transmission in an amount effective to block afferent neuron transmission in a subject; and a pharmaceutically acceptable carrier suitable for transdermal delivery of the compound.

Other features and advantages of the invention will be apparent from the following detailed description and claims.

BRIEF DESCRIPTION OF THE DRAWINGS

FIG. 1 is an evaluation form used in evaluating an embodiment of the present invention.

FIG. 2 is a table depicting the results from clinical experiments using compositions of the invention.

DETAILED DESCRIPTION OF THE INVENTION

The present invention provides a transdermal composition suitable for treatment of pain in a subject. The transdermal composition includes an amine containing compound having biphasic solubility in an amount effective to treat pain in a subject; and a pharmaceutically acceptable carrier suitable for transdermal delivery of the amine containing compound having biphasic solubility.

As used herein, the term "subject" includes a mammal, such as a human, a horse, a pig, a cow, a mouse, a rat, a rabbit, or a goat. In preferred embodiment, the subject is a human.

As used herein, the term "pain" is art recognized and includes a bodily sensation elicited by noxious chemical, mechanical, or thermal stimuli, in a subject, e.g., a mammal such as a human. The term "pain" includes chronic pain, such as lower back pain; pain due to arthritis, e.g., osteoarthritis; joint pain, e.g., knee pain or carpal tunnel syndrome; myofascial pain, and neuropathic pain. The term "pain" further includes acute pain, such as pain associated with muscle strains and sprains; tooth pain; headaches; pain associated with surgery; or pain associated with various forms of tissue injury, e.g., inflammation, infection, and ischemia.

As used herein, the term "amine containing compound having biphasic solubility" includes compounds having at least one amine moiety and having sufficient lipid solubility (e.g., solubility in polar solvents such as ethanol, ethoxydiglycerol, ethoxydiglycol, chloroform, benzene, and the like) such that the compound passes through the stratum corneum, and has sufficient aqueous solubility to be active in the aqueous environment of the dermis and the underlying tissue.

Transdermal compositions of the present invention include an amine containing compound having biphasic solubility in an amount effective to treat pain in a subject. As used herein, the terms "amount effective to treat pain in a subject" and "effective amount" are used interchangeably herein and include an amount effective, at dosages and for periods of time necessary, to achieve the desired result, e.g., sufficient to treat pain in a subject. An effective amount of an amine containing compound or a pharmaceutical compound as defined herein may vary according to factors such as the disease state, age, and weight of the subject, and the ability of the amine containing compound or pharmaceutical compound to elicit a desired response in the subject. Dosage regimens may be adjusted to provide the optimum therapeutic response. An effective amount is also one in which any toxic or detrimental effects of the amine containing compound having biphasic solubility or pharmaceutical compound are outweighed by the therapeutically beneficial effects.

The transdermal compositions of the invention can further include an agent which enhances the activity of the amine containing compound having biphasic solubility. As used herein, an "agent which enhances the activity of the amine containing compound having biphasic solubility" includes an agent which enhances the pharmacological activity of the amine containing compound hiving biphasic solubility (e.g., the ability of the amine containing compound to treat pain), or enhances the transdermal delivery of the amine containing compound having biphasic solubility (e.g., the ability of the amine containing compound to cross the stratum corneum), or enhances both the pharmacological activity and the transdermal delivery of the amine containing compound. Examples of agents which enhance the activity of the amine containing compound having biphasic solubility, include muscle relaxants, described in further detail below.

As used herein, the term "transdermal" composition includes compositions capable of passing through the stratum corneum of a subject. The term transdermal further includes compositions capable of passing through the epidermis of a subject, compositions capable of passing through the dermis of a subject, and compositions capable of passing through the hypodermis of a subject. In preferred embodiments, the term transdermal includes compositions capable of passing through the skin of a subject and reaching the underlying tissues and organs.

As used herein, the term "transdermal delivery" includes delivery of, for example, a compound through the stratum corneum of a subject. The term transdermal delivery further includes delivery of, for example, a compound through the epidermis of a subject, delivery of, for example, a compound through the dermis of a subject, and delivery of, for example, a compound through the hypodermis of a subject. In preferred embodiments, the term transdermal delivery includes delivery of, for example, a compound through the skin of a subject to the underlying tissues and organs.

The present invention further features a transdermal composition for treatment of pain in a subject which includes a compound capable of blocking afferent neuron transmission in an amount effective to block afferent neuron transmission in a subject; and a pharmaceutically acceptable carrier suitable for transdermal delivery of the compound.

As used herein, the term "compound capable of blocking afferent neuron transmission" includes a compound which is capable of blocking the ability of an afferent neuron, i.e., a sensory neuron, to carry an impulse toward the central nervous system.

Various aspects of the invention are described in further detail in the following subsections:

Amine Containing Compounds Having Biphasic Solubility

Amine containing compounds having biphasic solubility for use in the transdermal compositions of the invention include antidepressant compounds, antiepileptic compounds, anticonvulsant compounds, and sodium channel blockers. As used herein, the term "antidepressant compounds" includes compounds capable of alleviating the symptoms of depression. Examples of antidepressant compounds include all tricyclic antidepressants (e.g., amitriptyline, dothiepin, or lofepramine), bupropion (sold under the trade name Wellbutrin), reboxetine (sold under the trade name Edronax), nefazodone (sold under the trade name Serzone) and trazone (sold under the trade name Desyrel). Antidepressant compounds are described in, for example, the 1998 SIGMA catalogue and the "The Merck Index", 12th Ed., Budavari et al., eds., Merck & Co., Inc., Rahway, N.J., 1996, the contents of which are incorporated herein by reference.

In one embodiment of the present invention, the antidepressant compounds of the present invention contain a tricyclic moiety. Therefore, in a preferred embodiment, a transdermal composition of the present invention includes a tricyclic antidepressant compounds. Exemplary tricyclic antidepressants include adinazolam, amitriptylinoxide, amoxapine, clomipramine, demexiptiline, dimetacrine, dothiepin, doxepin, imipramine N-oxide, iprindole, lofepramine, melitracen, metapramine, noxiptilin, pizotyline, propizepine, quinupramine, tianeptine, and trimipramine. A particularly preferred tricyclic antidepressant for use in the compositions of the invention is doxepin.

Tricyclic antidepressant compounds are described in, for example, "Guide to Clinical Neurology" by J. P. Mohr et al. (Churchill Livingstone, 1995), the contents of which are incorporated herein by reference.

Preferably, the tricyclic antidepressant compound is selected from the group consisting of doxepin, trimipramine, other tricyclics having biphasic solubility, and combinations thereof. When combined with other compounds, such as an agent which enhances the activity of the amine containing compound, e.g., a muscle relaxant, and/or an anti-inflammatory compound, e.g., a nonsteroidal anti-inflammatory compound, as discussed below, the tricyclic antidepressant preferably constitutes from about 1% by weight (% by wt.) to about 30% by wt. of the total amount of the pharmaceutical, more preferably from about 3% by wt. to about 15% by wt., and most preferably from about 5% by wt. to about 13% by wt.

The amine containing compounds having biphasic solubility used in the transdermal compositions of the invention further include antiepileptic compounds. As used herein, the term "antiepileptic compound" includes compounds capable of alleviating the symptoms of epilepsy. Exemplary antiepileptic compounds for use in the compounds of the invention include lamotrigine, felbamate, and carbamazepine. Preferably, the antiepileptic compound is selected from the group consisting of lamotrigine, felbamate, carbamazepine, and combinations thereof. When combined with other compounds, such as an agent which enhances the activity of the amine containing compound, e.g., a muscle relaxant, and/or an anti-inflammatory compound, e.g., a nonsteroidal anti-inflammatory compound as discussed below, the antiepileptic compound constitutes from about 1% by wt. to about 30% by wt. of the total amount of the pharmaceutical, more preferably from about 3% by wt. to about 20% by wt., and most preferably from about 5% by wt. to about 15% by wt. Antiepileptic compounds are described in, for example, the 1998 SIGMA catalogue, the "The Merck Index", 12t:h Ed., Budavari et al., eds., Merck & Co., Inc., Rahway, N.J., 1996, and the "Guide to Clinical Neurology" by J. P. Mohr et al. (Churchill Livingstone, 1995) the contents of which are incorporated herein by reference.

In another aspect of the present invention, the amine containing compounds having biphasic solubility of the present invention include anticonvulsant compounds. As used herein, the term "anticonvulsant compound" includes compounds capable of alleviating the symptoms of convulsion, i.e., the violent involuntary tetanic contractions of an entire group of muscles. Exemplary anticonvulsant compounds which for use in the compositions of the invention include felbamate, lamotrigine and carbamazepine. Preferably, the anticonvulsant compound is selected from the group consisting of felbamate, lamotrigine, and combinations thereof. When combined with other compounds, such as an agent which enhances the activity of the amine containing compound, e.g., a muscle relaxant, and/or an anti-inflammatory compound, e.g., a nonsteroidal anti-inflammatory compound as discussed below, the anticonvulsant compound constitutes from about 1% by wt. to about 30% by wt. of the total amount of the pharmaceutical, more preferably from about 3% by wt. to about 20% by wt., and most preferably from about 5% by wt. to about 15% by wt. Anticonvulsant compounds are described in, for example, the 1998 SIGMA catalogue, the "The Merck Index", 12t:h Ed., Budavari et al., eds., Merck & Co., Inc., Rahway, N.J., 1996, and the "Guide to Clinical Neurology" by J. P. Mohr et al. (Churchill Livingstone, 1995) the contents of which are incorporated herein by reference.

In yet another aspect of the present invention, the amine containing compounds having biphasic solubility of the present invention include adrenergic agonist compounds. Preferably, the adrenergic agonist compound is tizanidine. When combined with other compounds, such as a muscle relaxant and/or nonsteroidal anti-inflammatory compound as discussed below, the adrenergic agonist compound constitutes from about 1% by wt. to about 30% by wt. of the total amount of the pharmaceutical, more preferably from about 3% by wt. to about 20% by wt., and most preferably from about 5% by wt. to about 15% by wt. Adrenergic agonist compounds are described in, for example, the 1998 SIGMA catalogue, the "The Merck Index", 12t:h Ed., Budavari et al., eds., Merck & Co., Inc., Rahway, N.J., 1996, and the "Guide to Clinical Neurology" by J. P. Mohr et al.(Churchill Livingstone, 1995) the contents of which are incorporated herein by reference.

The amine containing compounds having biphasic solubility used in the transdermal compositions of the invention further include sodium channel blockers. As used herein, the term "sodium channel blockers" includes compounds which are capable of blocking the activity of a sodium channel. Examples of sodium channel blockers include tetrodoxin, flecainide, disopyramide, and terfenadine. Sodium channel blockers are described in, for example, the 1998 SIGMA catalogue, the "The Merck Index", 12t:h Ed., Budavari et al., eds., Merck & Co., Inc., Rahway, N.J., 1996, and the "Guide to Clinical Neurology" by J. P. Mohr et al.(Churchill Livingstone, 1995) the contents of which are incorporated herein by reference.

Whenever nerves are damaged, for example, by trauma, by diseases such as diabetes, herpes zoster, or late-stage cancer, or by chemical injury (e.g., as an untoward consequence of agents including the false-nucleoside anti-HIV pharmaceuticals), neural pain circuits rewire themselves, anatomically and/or biochemically. Thus, following an injury, new sodium channels are formed which is believed to constitute the basis for chronic pain development. Through a similar action in the dorsal root ganglia, chronic regional pain syndromes may develop. Each time one of these sodium channels depolarizes, a nerve impulse originates. Because there are so many sodium channels, there may be a constant cascade of nerve impulses, causing allodynia, burning sensations, and/or dysesthesias. It is believed that some chronic pains may be mediated through sodium channels in nerve cells. Thus, it is believed that amine containing compounds having biphasic solubility which can block sodium channels may also be used in the transdermal compositions of the invention.

In one embodiment of the invention, the amine moiety of the amine containing compounds having biphasic solubility of the present invention may function similar to a sodium ion upon entry into the sodium channel of a nerve cell membrane. A non-polar moiety, which is preferably present in the amine containing compound having biphasic solubility of the present invention may interact with the nerve cell membrane, perhaps through Van der Waals forces. In such cases, it is believed that the presence of the non-polar moiety prevents or inhibits a complete uptake of the amine containing compound having biphasic solubility through the nerve cell membrane. It is believed that one or more these interactions prevent or reduce the amount and/or the rate of depolarization and ion exchange involved in stimulus conduction, thereby decreasing pain sensation.

The amount of an amine containing compound having biphasic solubility useful in relieving pain transdermally may be determined by methods known in the art, and typically ranges from about 1 mg to about 300 mg per subject per dose, preferably from about 5 mg to about 100 mg per subject per dose, and more preferably from about 10 mg to about 50 mg per subject per dose, depending on a variety of factors including the particular amine containing compound having biphasic solubility used, whether the area of transdermal application is the site of action, and the intended size of the site of action. In a preferred embodiment, the amount of an amine containing compound having biphasic solubility useful in relieving pain transdermally, is 5, 10, 15, 20, 25, 30, 35, 40, 45, 50, 55, 60, 65, 70, 75, 80, 85, 90, 95, 100 mg, 150 mg, 200 mg, 250 mg, or 300 mg per subject per dose.

Muscle Relaxants

Transdermal compositions of the present invention may also include a muscle relaxant. As used herein, the term "muscle relaxant" includes compounds which facilitate or enhance the relaxation of muscles (e.g., provide relief from muscle spasm) and, thus, facilitate or enhance the transdermal delivery of the transdermal compositions of the invention. Exemplary muscle relaxants include both skeletal muscle relaxants and smooth muscle relaxants such as anticholinergics, antispasmodics, bronchodilators, and vasodilators. Muscle relaxants are described in, for example, the 1998 SIGMA catalogue, the "The Merck Index", 12t:h Ed., Budavari et al., eds., Merck & Co., Inc., Rahway, N.J., 1996, pp. THER-1 to THER-28, and the "Guide to Clinical Neurology" by J. P. Mohr et al. (Churchill Livingstone, 1995) the contents of which are incorporated herein by reference. Preferably, the muscle relaxant is selected from the group consisting of guaifenesin, benzodiazepines (e.g., clozapine or diazopam), chlorzoxazone, dantrolene sodium, metaxalone, carisoprodol, other muscle relaxants having biphasic solubility, and combinations thereof More preferably, the muscle relaxant is selected from the group consisting of guaifenesin, chlorzoxazone, and combinations thereof. A preferred muscle relaxant for use in the compositions of the invention is guaifenesin.

Preferably the muscle relaxant has biphasic solubility. Preferably the muscle relaxant, when present in the pharmaceutical composition, constitutes from about 1% by wt. to about 30% by wt. of the total amount of the pharmaceutical, more preferably from about 3% by wt. to about 20% by wt., and most preferably from about 5% by wt to about 15% by wt.

Anti-Inflammatory Compounds

The transdermal compositions of the present invention may also include an anti-inflammatory compound. As used herein, the term "anti-inflammatory compound" includes a compound which is capable of reducing cell migration, caused by ischemic and trauma associated events, and therefore reduces edema formation to thereby provide pain relief. Preferably, the anti-inflammatory compound is a nonsteroidal anti-inflammatory compound (i.e., NTHE) including ketoprofen. Anti-inflammatory compounds, e.g., NTHEs, are described in, for example, the 1998 SIGMA catalogue, the "The Merck Index", 12t:h Ed., Budavari et al., eds., Merck & Co., Inc., Rahway, N.J., 1996, pp. THER-1 to THER-28, and the "Guide to Clinical Neurology" by J. P. Mohr et al. (Churchill Livingstone, 1995) the contents of which are incorporated herein by reference. Preferably, the NTHE is selected from the group consisting of celecoxib, etodolac, mefanamic acid, nabumetone, salsalate, naproxen, Vioxx®, COX-2 NTHEs having biphasic solubility, and combinations thereof.

More preferably, the NTHE is selected from the group consisting of celecoxib, etodolac, naproxen, COX-2 NTHEs having biphasic solubility, and combinations thereof. Preferably, the NTHE has biphasic solubility. The NTHE, when present in the transdermal composition, preferably, constitutes from about 1% by wt. to about 30% by wt. of the total amount of the pharmaceutical, more preferably from about 3% by wt. to about 30% by wt., and most preferably from about 5% by wt. to about 30% by wt.

Dosages

The concentration as well as the quantity of the amine containing compounds having biphasic solubility, the agents which enhance the activity of the amine containing compounds, e.g., the muscle relaxants, and the anti-inflammatory compounds can be varied independently in order to achieve the desired effect. For example, higher concentrations of the amine containing compounds having biphasic solubility, the muscle relaxants, and the anti-inflammatory compounds contained in a dosage form of decreased viscosity may result in an analgesic with fast onset and short duration. High concentrations of the amine containing compounds having biphasic solubility, the muscle relaxants, and the anti-inflammatory compounds contained in a dosage form of increased viscosity may result in potent analgesic with fast onset and long duration. Low concentrations of the amine containing compounds having biphasic solubility, the muscle relaxants, and the anti-inflammatory compounds in a dosage form of decreased viscosity may result in mild analgesic with longer onset and short duration. Low concentrations of the amine containing compounds having biphasic solubility, the muscle relaxants, and the anti-inflammatory compounds contained in a dosage form of increased viscosity may have mild analgesic properties with longer onset and longer duration. The ability to vary the concentration of the amine containing compounds having biphasic solubility, the muscle relaxants, and the anti-inflammatory compounds from very low to high of the total composition, combined with the ability to coat thin (about 0.1 mm) or thick (about 0.5 mm) enables the practitioner of the invention to vary the dosage of the system as needed for particular level of pain and anatomical sites of interest. It should be appreciated, however, that, onset time as yell as duration of analgesic effect of the transdermal composition of the present invention will vary from subject to subject as well as on the basis of the site of application, and properties of the amine containing compounds having biphasic solubility, the muscle relaxants, and the anti-inflammatory compounds.

Generally, the concentration of the amine containing compounds having biphasic solubility, the muscle relaxants, and the anti-inflammatory compounds can range, on a weight basis, from about 1% to about 30% of the total composition, preferably from about 3% to about 20%, and more preferably from about 5% to about 15%.

Pharmaceutically Acceptable Carriers

The transdermal compositions of the present invention also includes a pharmaceutically acceptable carrier which is capable of transdermal delivery of the amine containing compound having biphasic solubility. As used herein, the term "pharmaceutically acceptable carrier suitable for transdermal delivery" includes a carrier capable of delivering the amine containing compound transdermally as defined above. Suitable carriers for transdermal delivery of pharmaceuticals are described in U.S. Pat. No. 5,446,070, the contents of which are incorporated herein by reference. Briefly, pharmaceutically acceptable carriers of the present invention include any suitable finite (i.e, solid) or non-finite (i.e, non-solid, such as liquid or semi-liquid) carrier including liquids, semi-liquids or solid carriers, such as a bioadhesive. Thus, the amine containing compounds having biphasic solubility may be admixed with a pharmaceutically acceptable carrier such as a cream, gel, emulsion, lotion, salve, paste, plaster, ointment, spray solution, or any other "non-finite" carrier known in the art of pharmaceutical delivery. For example, the base of a non-finite carrier may be lipid including phospholipids such as lecithins; fatty oils; lanolin; vasoline; paraffins; glycols; higher fatty acids; and higher alcohols.

The term "bioadhesive" as used herein includes an adhesive which attaches to a biological surface such as skin or mucosal tissue. Preferably, the bioadhesive of the present invention is self-adhesive in that it attaches to the site of interest without the need to reinforce its attachment by way of another adhesive. Suitable bioadhesive include natural or synthetic polysaccharides such as cellulose derivatives including methylcellulose, cellulose acetate, carboxymethylcellulose, hydroxyethylcellulose and the like; pectin; a mixture of sulfated sucrose and aluminum hydroxide; hydrophilic polysaccharide gums including natural plant exudates, such as karaya gum, ghatti gum, tragacanth gum, xanthan gum, jaraya gum and the like; seed gums including guar gum, locust bean gum, psillium seed gum and the like; and lecithins such as soya lecithin. In addition to the above ingredients, compositions of the present invention may also include other ingredients such as various pharmaceutically acceptable additives available to those skilled in the art. These additives include binders, stabilizers, preservatives, flavorings, fiances, and pigments.

In another embodiment, the pharmaceutically acceptable carrier of the present invention includes van pen cream (cetyl alcohol, stearyl alcohol, steric acid, gllycerol monosterate, isopropyl myristate, soya lecithin, BHT alcohol 95%, simethicone, sodium hydroxide 30% solution, polyoxyl stearate, edetate disodium 5%, purified water, urea).

Other Pharmaceutical Compounds

In another aspect, the invention features a transdermal composition suitable for transdermal delivery, which includes a therapeutically effective amount of a pharmaceutical compound (e.g., a serotonin specific reuptake inhibitor, a mood stabilizing compound, a dopamine compound, a compound suitable for treating attention deficit hyperactivity disorder, a compound suitable for treating hypertension and akathisia, an analgesic compound, or a compound used in the treatment of impotence) and a pharmaceutically acceptable carrier suitable for transdermal delivery of the pharmaceutical compound.

As used herein, the term "pharmaceutical compound" includes compounds suitable for treating a targeted condition and capable of being delivered in active form, in vivo. Examples of pharmaceuticals include drugs, enzymes, chemical compounds, combinations of chemical compounds, biological macromolecules and analogs thereof. Examples of pharmaceutical compounds are described in detail below.

In one embodiment of the invention, the pharmaceutical compound is a serotonin specific reuptake inhibitor (SSRI). SSRIs are commonly prescribed for patients with diagnoses of mood disorders, some forms of anxiety disorder (particularly panic disorder), obsessive compulsive disorders, some forms of menopausal disorders, and eating disorders (especially bulimia nervosa). Examples of such SSRIs include sertraline (sold under the trade name Zoloft), paroxetine (sold under the trade name Paxil), fluoxetine (sold under the trade name Prozac), venlafaxine (sold under the trade name Effexor), and fluvoxamine (sold under the trade name Luvox).

In another embodiment of the invention, the pharmaceutical compound is a mood stabilizing medication, such as carbamazepine (sold under the trade name Tegretol) and valproic acid (sold under the trade name Depakote). These agents are used frequently in psychiatric practice as either augmentation medications (to render antidepressants more effective) or as anti-manic medications in the treatment of bipolar mood disorder. Mood stabilizing medications are also used in neurologic practice for the treatment of seizure disorders and for the treatment of certain pain disorders.

In yet another embodiment of the invention, the pharmaceutical compound is a compound used for treating Attention Deficit Hyperactivity Disorder (ADHD), one example of which is permoline, sold under the trade name Cylert. Permoline is a medication that is used in the treatment of Attention Deficit Hyperactivity Disorder in children and adults. It is practically insoluble in water, but soluble in ethylene glycol and lipids, making it a good candidate for transdermal administration In a further embodiment of the invention, the pharmaceutical compound is a dopamine compound, used for treating Parkinson's disease, examples of which are pergolide, sold under the trade name Permax and bromocriptine mesylate, sold under the trade name Parlodel.

In yet another embodiment of the invention, the pharmaceutical compound is a compound used for treating hypertension and akathisia, one example of which is propranalol, sold under the trade name Inderal.

In yet a further embodiment of the invention, the pharmaceutical compound is a compound used in the treatment of impotence such as sildenafil, sold under the tradename Viagra. It is believed that transdermal administration of sildenafil may be useful, for at least some subjects, as compared to oral administration which has been found, in at least some situations, to be associated with gastrointestinal side effects.

Methods For Preparing The Transdermal compositions

Another embodiment of the present invention provides a method for preparing the above described transdermal compositions, by admixing a therapeutically effective amount of the amine containing compound having biphasic solubility, optimally an agent which enhances the activity of the amine containing compound, e.g., a muscle relaxant, optimally an anti-inflammatory compound with the carrier suitable for transdermal delivery of the amine containing compound.

In one embodiment of the present invention, a transdermal composition is prepared by dispersing or dissolving crushed tablets, capsules or other preparation(s) of the amine containing compound having biphasic solubility, the muscle relaxants, and the anti-inflammatory compounds, which were intended for oral delivery, in a gel formed of soya lecithin and isopropyl palmitate or isopropyl myristate, alcohol, or ethoxy diglycol. In another embodiment of the present invention, Pluronic gel, formed of Pluronic such as Pluronic F127, potassium sorbate and water is used.

In a particular embodiment of the present invention, a transdermal composition including a combination of doxepin with guaifenesin is useful for treating pain. It is believed that transdermal administration of such combination can be advantageous, for at least some patients, as compared to oral administration, because higher local pharmaceutical concentrations at the site(s), e.g., of injury, can be achieved yielding an improved therapeutic response without systemic side effects such as weight gain, drowsiness, gastrointestinal upset and/or other known side effects of these pharmaceuticals.

Methods For Use

In one embodiment, the invention feature methods for treating pain in a subject in which the subject is contacted with a transdermal composition including an amine containing compound having biphasic sole in an amount effective to treat pain in the subject; and a pharmaceutically acceptable carrier suitable for transdermal delivery of the amine containing compound to thereby treat pain in the subject In a preferred embodiment, the transdermal composition is applied to the skin of the subject as often as needed for the alleviation of pain. For example, the transdermal composition may be applied daily, weekly, monthly, yearly, for a length of time sufficient to alleviate pain.

Detailed examples of the preparation are provided below, along with examples of results obtained from transdermal administration to human patients. Preferably, a gel preparation is applied to the skin at the site or sites of pain. Patients can be evaluated by means of a structured evaluation form, e.g., completed at a frequency of at least one time per week. Evaluation of patients are for the present symptoms as well as any side effects from currently administered medications. This makes it possible to note changes on an ongoing basis.

Compositions of the invention can be self-administered doses in the form of a gel applied to the skin by the patient, or be implemented by providing a transdermal preparation in premeasured doses preferably in connection with an adhesive or other covering or patch so that the dosage may be administered e.g., by placing the adhesive patch on the skin of the patient. Although some embodiments of the invention have been described in connection with positioning the pharmaceutical gel on the arm of a patient, other positioning on the skin of a patient can also be used. Because, depending on the formulation, speed or duration of transdermal delivery may vary as function of skin location, in one embodiment the location of the skin to which the pharmaceutical is applied is selected so as to relatively increase or decrease the delay, speed, duration, or rate of delivery of the pharmaceutical, either with respect to a particular tissue or systemically.

For example, when a rapid rise in blood serum levels is desired, a placement which enhances delivery rate, such as behind the ear, can be used. When it is desired to enhance dose or delivery rate locally, the transdermal formulation may be positioned adjacent the desired treatment area. Membranes or matrices, such as a polymer matrix, may be used to limit or control delivery rates. In addition to transdermal gel or patch delivery, delivery of the transdermal or aerosol formulation can be achieved, e.g. by administration as nose drops, eardrops, eyedrops and/or suppositories.

In one embodiment, medications dispensed in transdermal gel form will be dispensed in unit doses, such as blister packs. The gel will be extruded from the blister pack, and rubbed on the administration site. The dosage will be adjusted by varying the number of unit dose applied. This will ensure accurate dosimetry and will avoid contamination of the gel.

Methods For Selecting A Compound Suitable For Treating Pain

In a further aspect, the invention features a method for selecting a compound suitable for treating pain in a subject. The method includes transdermally administering an amine containing compound having biphasic solubility to a subject; and determining whether pain is treated in the subject to thereby select a compound suitable for treating pain in a subject. In a preferred embodiment, the method can further include modeling the compound using a computer equipped with a three-dimensional chemical structure modeling program (e.g., Molecules-3D Professional Edition, version 2.60, copyright 1991–1998, Molecular Arts Corp., © 1994–1998 WCB/McGraw Hill); and determining whether the three-dimensional chemical structure of the compound possesses sufficient characteristics to be useful as a sodium channel blocker, thereby selecting a compound suitable for treating pain in a subject.

The effectiveness of the amine containing compound having biphasic solubility to treat pain can be tested in vitro or in vivo. An animal model for pain, e.g., such as the one described in Kral M. G. et al. (1999) *Pain* 81(1–2):15–24 can, for example, be used for testing such compounds.

This invention is further illustrated by the following examples which should not be construed as limiting. The contents of all references, patents and published patent applications cited throughout this application, as well as the Figures are incorporated herein by reference.

EXAMPLES

Example 1

One hundred grams of lecithin soya (granular) and 0.66 grams sorbic acid NF-FCC powder) were dispersed in 100 grams (117 milliliters (mL)) of isopropyl palmitate NF and allowed to stand overnight. Approximately 220 milliliters of lecitbin-isopropyl palmitate in a form of a liquid of a syrup consistency was formed.

Example 2

One hundred grams of lecithin soya (granular) and 0.66 grams sorbic acid (NF-FCC powder) is dispersed in 100 grams (117 milliliters) of isopropyl myristate NF and allowed to stand overnight. Approximately 220 milliliters of lecithin-isopropyl myristate in a form of a liquid of a syrup consistency was formed.

Example 3

A beaker was prepared by treasuring to a volume of 100 milliliters. It was considered important to measure the volume accurately rather than using beaker markings. An amount of Pluronic F127 NF (20 grams for a 20 percent gel, 30 grams for a 30 percent gel, 40 grams for a 40 percent gel) was mixed with 0.3 grams potassium sorbate NF. Refrigerated purified water was added in an amount sufficient to bring the volume to 100 milliliters. When all of the granules had been wet the gel was refrigerated. Solution took place upon cooling, taking 12 to 24 hours. The resulting 100 milliliters of Pluronic gel was kept refrigerated, since the gel will solidify at room temperature.

Example 4

Nine grams of carbamazepine in tablet form was ground in mortar and pestle. 4.3 milliliters of ethoxy diglycol was added and mixed to form a creamy paste. 13.2 milliliters of soya lecithin was added and mixed until smooth. The resulting 24 cc of solution was put into a 60 cc syringe. About 36 cc Pluronic F127 gel 20 percent (made according to Example 3) was placed in another syringe. The material was mixed well between syringes to yield 60 cc of carbamazepine organogel having a strength of 150 milligrams (mg) per milliliter. In some cases, the mixture was run through an ointment mill to reduce particle size.

Example 5

Sixty 100 milligram tablets of buprorion were ground and strained to form a fine powder. The buprorion powder was dissolved in 30 cc purified water, placed in a filter and washed with 10 to 20 cc purified water. The filtrate was used to make a 20 percent Pluronic gel using the procedures from Example 3, substituting filtrate for an equivalent volume of water, and stored in a refrigerator. Thirteen milliliters of soya lecithin was mixed with one-half the buprorion Pluronic gel and mixed between syringes to form a first batch. Thirteen milliliters of soya lecithin was mixed with the second half of the buprorion Pluronic gel and mixed between syringes to form a second batch. To each batch was added sufficient Pluronic gel F127 (made according to example 3) to yield a total of two 60 cc batches of buprorion HCl organogel having a strength of 15 milligrams per milliliter.

Example 6

600 milligrams of fluoxetine HCl (in the form of thirty 20 milligram capsules) was placed in a beaker and dissolved in approximately 18 cc of 95 percent ethyl alcohol. The solution was filtered through a filter funnel using fine filter paper. The residue was washed with 95 percent alcohol. The filtrate was heated, maintaining a temperature less than 85° C., to evaporate the alcohol to concentrate to 1 to 2 milliliters. 600 milligrams of isopropyl palmitate was combined with 600 milligrams of soya lecithin (granular), set aside and allowed to liquefy. Upon liquefaction, a thick syrupy consistency was obtained. 1.2 grams of the mixture was drawn into a 10 milliliter syringe and the alcoholic solution of fluoxetine HCl was drawn into another syringe. The two syringes were attached together with a Luer-Luer adapter and the gel was thoroughly mixed. All of the organogel was then transferred into one syringe and the empty syringe was disconnected. Sufficient quantity of 20 percent Pluronic F127 gel (formed as described in Example 3) was drawn into the empty syringe to make a total of 6 milliliters when added to the volume in the other syringe. A Luer-Luer adapter was attached and the contents of the two syringes was remixed until a smooth creamy mixture was obtained. All the mixture was transferred into one syringe, the empty syringe was removed and the Luer-Luer adapter was removed.

A Luer-oral adapter was attached to the mixture and transferred to six 1 milliliter oral syringes, was filled with 1 milliliter of the gel. In this way, each syringe contained five 20 milligram doses, or ten 10 milligram doses to yield a total of 60 doses of fluoxetine in lecithin organogel having a strength of 10 milligrams per 0.1 milliliters.

Example 7

Twelve 250 milligram tablets of nefazadone were crushed in a mortar and pestle and put through a strainer. 4.8 milliliters of ethoxy diglycol (8 percent) was added and mixed. In cases in which all particles were not dissolved, 2 milliliters of Pluronic were added and mixed. 13.6 milliliters of soya lecithin were added and mixed. The resulting mixture was put into syringes with a Luer adapter and mixed well. Sufficient Pluronic F127 gel, prepared according to Example 3, was added to achieve a volume of 60 cc and mixed well to yield 60 cc of nefazadone organogel having a strength of 50 milligrams per milliliter.

Example 8

Thirty 40 milligram tablets of paroxetine were crushed and run through a strainer, discarding green coating material. 4.8 milliliters of ethoxy diglycol was added to the powder and mixed in a mortar and pestle. Forty milliliters of Pluronic F127 gel 20 percent, formed according to Example 3, was added in graduated amounts to the powder and mixed until smooth using a spatula. 13.2 milliliters of soya lecithin was added and mixed well and the resulting material placed into syringes and sufficient quantity of Pluronic gel was added to bring the volume to 60 milliliters. In those such cases where particle size of the resulting material was too large, the cream was run through an ointment mill to yield 60 milliliters of paroxetine organogel having a strength of 20 milligrams per milliliter.

Example 9

Thirty 100 milligram tablets of sertraline were crushed into a fine powder and strained, discarding the yellow coating. Sufficient amount of Pluronic F127 gel 20 percent (formed according to Example 3) was added to achieve a volume of 38 milliliters and mixed well in a mortar and pestle until a smooth cream was achieved. This material was placed into syringes and mixed between the syringes to obtain a compact cream. 13.2 milliliters of soya lecithin was added and mixed well between the syringes using about 20 pumps. Sufficient quantity of Pluronic F127 gel 20 percent was added to yield 60 milliliters of sertraline gel having a strength of 15 milligrams per milliliter.

Example 10

Venlafaxine hydrochloride has a solubility in water of 572 mg/mL (adjusted to ionic strength of 0.2 M with sodium chloride). Forty-five 100 milligram tablets of venlafaxine were crushed and put through a strainer. The powder was dissolved in 15 cc purified water, the solution placed into a filter and washed with 10 cc purified water. The filtrate was used to make a 20 percent Pluronic gel using the procedures of Example 3 (substituting the filtrate for an equivalent amount of water) and placed into a refrigerator overnight 13.2 milliliters of soya lecithin were drawn into a syringe with a Luer loc. The venlafaxine Pluronic gel was drawn into another syringe coupled to the first syringe and mixed well. Sufficient Pluronic F127 gel was added to achieve a volume of 60 cc with a strength of 75 mg. per cc.

Example 11

15 grams of sodium valproate (Depakote) was ground in mortar and pestle. 4 mL of ethoxy diglycol was added and mixed well to form a creamy paste. 19.8 mL of soya lecithin was added and mixed until smooth. The resulting 24 cc of solution was put into 2 syringes with a Luer Loc and mixed well. The mixture was divided so that half is in each syringe. Using another 60 cc syringe, Pluronic 30% gel was added to each to bring each syringe to a volume of 45 mL.

Example 12

Paroxetine hydrochloride has a solubility in water of 5.4 mg/mL. Paroxetine (Paxil) gel was prepared, according to the procedures of example 8. A dosage of 40 mg per day was self-administered by a 59 year old male patient by application to the skin, for a period of at least 1 hour. No skin irritation was reported. After 210 days, blood was drawn and blood serum level of Paxil was determined to be 0 nanograms (ng) per mL, while typical reference levels are 49±26 ng/mL, indicating possible poor absorption or lab error. Clinical evaluation of the patient over a 210 day period of such transdermal administration indicated benefit to patient without GI side effects similar to that noted with oral preparation.

Example 13

Sertraline hydrochloride is slightly soluble in water and isopropyl alcohol and sparingly soluble in ethanol. Sertraline (Zoloft) gel was prepared, according to the procedures of example 9. A dosage of 100 mg per day was self-administered by a 54 year old female patient by application to the skin, for a period of at least 1 hour. No skin irritation was reported. After 19 days, blood was drawn and blood serum level of Zoloft was determined to be 5 ng/mL, while typical reference levels are 30–200 mg/mL indicating possible limited absorption or lab error.

Example 14

Fluoxetine hydrochloride has a solubility in water of 14 mg/mL. Fluoxetine (Prozac) gel was prepared, according to the procedures of example 6. A dosage of 20 mg per day was self-administered by a 54 year old female patient by application to the skin, for a period of at least 1 hour. No skin irritation was reported. After 7 days, blood was drawn and blood serum level of fluoxetine was determined to be 45 ng/ml, while the plasma level of the primary active metabolite norfluoxetin was also 45 ng/ml. There was evidence of patient benefit from the clinical evaluation.

Example 15

Carbamazepine is practically insoluble in water and soluble in alcohol and in acetone. Carbamazepine (Tegretol) gel was prepared, according to the procedures of example 4. A dosage of 400 mg per day was self-administered by a 55 year old male patient by application to the skin, for a period of at least 1 hour. No skin irritation was reported. After 120 days, blood was drawn and blood serum level of Tegretol was determined to be 4.6 micrograms ($\mu$g) per mL, while typical therapeutic levels are 4–10 11 $\mu$g/ml indicating good absorption. There were no GI side effects and the patient demonstrated clinical improvement.

Example 16

Carbamazepine (Tegretol) gel was prepared, according to the procedures of example 4. A dosage of 200 mg per day was self-administered by a 53 year old male patient by application to the skin, for a period of at least 1 hour. No skin irritation was reported. After 60 days, blood was drawn and blood serum level of Tegretol was determined to be 10.8 $\mu$g/mL, while typical therapeutic levels are 4–10 11 $\mu$g/mL indicating excellent absorption. There were no GI side effects and the patient demonstrated clinical improvement.

Example 17

Sertraline (Zoloft) gel was prepared, according to the procedures of example 9. A dosage of 50 mg per day was self-administered by a 53 year old male patient by application to the skin, for a period of at least 1 hour. No skin irritation was reported. After 63 days, blood was drawn and blood serum level of Zoloft was determined to be 23 ng/mL, while typical reference levels are 30–200 mg/mL. The patient demonstrated a good clinical response without GI side effects.

Example 18

Carbamazepine (Tegretol) gel was prepared, according to the procedures of example 4. A dosage of 200 mg per day was self-administered by a 47 year old male patient by application to the skin, for a period of at least 1 hour. No skin irritation was reported. After 91 days, blood was drawn and blood serum level of Tegretol was determined to be less than 0.5 $\mu$g/mL, while typical therapeutic levels are 4–10 $\mu$g/mL, indicating poor absorption, lab error, or patient non-compliance.

Example 19

Buprorion is highly soluble in water. Buprorion (Wellbutrin) gel was prepared, according to the procedures of example 5. A dosage of 100 mg per day was selfadministered by a 47 year old male patient by application to the skin, for a period of at least 1 hour. No skin irritation was reported. After 44 days, blood was drawn and blood serum level of Wellbutrin was determined to be less than 0.5 ng/mL, while typical therapeutic levels are 10–30 indicating poor absorption, lab error, or patient non-compliance.

Example 20

Fluoxetine gel was prepared, according to the procedures of example 6. Typically, a total daily adult dosage of fluoxetine as applied to the skin according to the present invention is between about 20 mg and 200 mg, more preferably between about 120 mg and about 200 mg. Dosages for non-adults and/or non-human mammals may need to be adjusted, e.g. proportionally to body weight A dosage of 20–60 mg per day was self-administered by 5 patients, including that of example 13 and also including a 44 year old male patient, a 53 year old female patient, a 47 year old male patient and a 36 year old female patient by application to the skin, for a period of at least 1 hour. No skin irritation or gastrointestinal side effects were reported. Clinical evaluation of the patients over a 30–180 day period of such transdermal administration indicated a clinical response ranging from complete remission of symptoms to moderate improvement.

Example 21

Fluoxetine gel was prepared, according to the procedures of example 6. A dosage of 80–160 mg per day was self administered by a 50 year old female by application to the skin, for a period of at least 1 hour. No skin irritation was reported. After 7 days at the 80 mg dosage level blood was drawn and the blood serum of fluoxetine was determined to be 34 ng/mL fluoxetine and 25 ng/mL norfluoxetine, while typical reference levels are 50–480 ng/mL, indicating good absorption. There was evidence of patient benefit from the clinical evaluation. The dosage was then increased to 160 mg per day and administered by the same method. After 7 days at the 160 mg dosage level blood was drawn and the blood serum level of fluoxetine was determined to be 90 ng/mL fluoxetine and 25 ng/mL norfluoxetine, indicating good absorption. There was evidence of increased patient benefit at this higher dosage level which correlated positively with the higher plasma level. The patient has been receiving the medication continuously for a period of 5 months.

Example 22

Fluoxetine gel was prepared, according to the procedures of example 6. A dosage of 80–160 mg/day was self administered by a 38 year old female by application to the skin, for a period of at least 1 hour. No skin irritation was reported. After 7 days at the 80 mg dosage level, blood was drawn and the blood serum level of fluoxetine was determined to be 25 ng/mL of fluoxetine and 25 ng/mL norfluoxetine. There was evidence of patient benefit from the clinical evaluation. The dosage was then increased to 160 mg per day and administered by the same method.

Example 23

Sertraline (Zoloft) gel was prepared, according to the procedures of example 9. A dosage of 50–200 mg per day was self-administered by 6 patients, including those of examples 12 and 16 and also including a 60 year old male patient, a 53 year old male patient, a 48 year old male patient, a 38 year old male patient and a 47 year old male patient, by application to the skin, for a period of at least 1 hour. No skin irritation or gastrointestinal side effects were reported. Clinical evaluation of the patients over a 7–90 day period of such transdermal administration indicated responses ranging from complete resolution of depression to no noticeable response.

Example 24

Carbamazepine (Tegretol) gel was prepared, according to the procedures of example 4. A dosage of 200–400 mg per day was self-administered by 6 patients, including those of examples 14, 15 and 17, and also including a 48 year old female patient, a 48 year old male patient and a 54 year old female patient, by application to the skin, for a period of at least 1 hour. No skin irritation or gastrointestinal side effects were reported. The clinical evaluation of the patients over a 30–300 day period of such transdermal administration indicated responses ranging from moderate improvement to no positive clinical response.

Example 25

Paroxetine (Paxil) gel was prepared, according to the procedures of example 8. A dosage of 20 mg per day was self-administered by the patient of example 12 as well as by a 15 year old female patient by application to the skin, for a period of at least 1 hour. No skin irritation was reported. Clinical evaluation of the patients over a 30–210 day period of such transdermal administration indicated equivocal clinical improvement of the depression which may (or may not) have been related to the transdermally administered Paxil.

Example 26

Five 150 mg tablets of amitriptyline were crushed and run through a strainer. The powder was put into syringes with a Luer Loc and mixed well with 2 mL ethoxy diglycol. About 6 mL Pluronic Gel 20% was added and mixed well. 6.6 mL Soya Lecithin was added and mixed well. This mixture was thinned to 30-mL total volume with Pluronic Gel 20% and mixed well. The resulting mixture having a strength of 25 mg/mL was placed in appropriate dispensing device.

Example 27

Amitriptyline (Elavil) gel was prepared, according to the procedure of example 26. A dosage of 25 mg per day was self-administered by a 47 year old male patient. Administration was by application to the skin, for a period of at least 1 hour. No skin irritation or gastrointestinal side effects were reported. Clinical evaluation of the patients over a 100 day period of such transdermal administration indicated an apparently good clinical response, comparable to that achieved with oral medication.

Example 28

Trazodone (Desyrel) gel was prepared, according to a procedure similar to that of example 7. A dosage of 50–150 mg per day was self-administered by 2 patients, including a 36 year old female patient and a 47 year old male patient. Administration was by application to the skin, for a period of at least 1 hour. No skin irritation or gastrointestinal side effects were reported. Clinical evaluation of the patients over a 42–90 day period of such transdermal administration indicated a good to excellent clinical response.

Example 29

Venlafaxine (Effexor) gel was prepared, according to a procedure similar to that of example 9. A dosage of 150–225 mg per day was self-administered by 2 patients, including a 54 year old female patient and a 55 year old male patient. Administration was by application to the skin, for a period of at least 1 hour. No skin irritation or gastrointestinal side effects were reported. Clinical evaluation of the patients over a 15–165 day period of such transdermal administration indicated a response ranging from no clinical improvement to mild clinical improvement.

Example 30

Propranolol (Inderal) gel was prepared, according to a procedure similar to that of example 8 to produce a gel having a strength of 40 mg of propranalol per mL of gel. A dosage of 80 mg per day was self-administered by 2 patients, including a 36 year old female patient and a 47 year old male patient. Administration was by application to the skin, for a period of at least 1 hour. No skin irritation or gastrointestinal side effects were reported. Clinical evaluation of the patients over a 100 day period of such transdermal administration indicated results comparable to those achieved with oral medication.

Example 31

Buproprion (Wellbutrin) gel was prepared, according to a procedure described in example 5. A dosage of 150–200 mg per day was self-administered by 3 patients, including that of example 18, and also including a 38 year old male patient and a 53 year old female patient. Administration was by application to the skin, for a period of at least 1 hour. No skin irritation or gastrointestinal side effects were reported. Clinical evaluation of the patients over a 5–45 day period of such transdermal administration indicated equivocal results.

Example 32

Valproic acid (Depakote) gel was prepared, according to a procedure similar to that of example 4. A dosage of 1000 mg per day was self-administered by a 38 year old male patient. Administration was by application to the skin, for a period of at least 1 hour. No skin irritation or gastrointestinal side effects were reported. Clinical evaluation of the patients over a 30 day period of such transdermal administration indicated results comparable to those achieved with oral medication.

Example 33

Valproic acid (Depakote) gel was prepared according to the procedure of example 11. A dosage of 500–1000 mg was self administered by two male patients, ages 41 and 49. Administration was by application to the skin, for a period of at least one hour. Significant skin irritation occurred with one patient, but no gastrointestinal side effects were reported. Clinical evaluation of the patients over a period of two months revealed improvement, but upon longer term follow-up it appeared that other factors may have been responsible. After 28 days, blood was drawn and a serum valproic acid level of 26 µg/mL was obtained for the 49 year old patient (while taking 250 mg twice daily), with a therapeutic reference range of 50–150 µg/mL. This indicated poor to fair absorption, and the dosage was raised to 500 mg twice daily, with a further improvement in clinical response. The 41 year old patient reported a good clinical response to an initial dosage of 250 mg adored twice daily, but a serum valproic acid level of only 1 µg/mL was obtained. The dosage was increased to 500 mg twice daily, and a similar serum valproic acid level was obtained. The disparity between the clinical response and the plasma level might be explained either by laboratory error or placebo effect.

Example 34

A gel containing reboxetine (sold under the trade name Edronax) is prepared according to a procedure similar to that described in example 5 but using reboxetine in place of boproprion. The resulting mixture will be self administered by patients by application to the skin for a period of at least I hour. No skin irritation or gastrointestinal side effects are expected. Clinical evaluation of patients over a 5–45 day period of such transdermal administration is expected to indicate a good response to treatment.

Example 35

Nefazodone (Serzone) gel was prepared, according to a procedure described in example 7. A dosage of 100 mg per day was self-administered by a 61 year old (male, female) patient. Administration was by application to the skin, for a period of at least 1 hour. No skin irritation or gastrointestinal side effects were reported. Clinical evaluation of the patients over a 21 day period of such transdermal administration indicated a good response to treatment.

Example 36

1 gram of permoline tablets are crushed in a mortar and then dissolved in propylene glycol, just sufficient to effect dissolution. 3 mL of propylene glycol or 95% ethyl alcohol is added to form a paste. 6.6 mL soya lecithin is added to the mixture in the mortar. The mixture is placed in two syringes with a Luer Loc and mixed thoroughly. Each syringe is filled to 30 mL Pluronic F127 20% gel and mixed between syringes to produce a mixture having a strength of 33 mg/mL. The mixture is put in an appropriate dispensing device.

Example 37

A 16-year-old female with an established diagnosis of Attention Deficit Disorder had been treated successfully with oral pemoline (Cylert) for about 6 months. To potentially decrease the risk of liver damage associated with long-term use, permoline prepared according to the procedure of example 36 will be administered transdermally, by application to the skin in the post auricular region for a period of at least one hour, at two sites, twice daily. No skin irritation is expected. The clinical results are expected to be comparable to those obtained with the oral medication, although the dosage may have to be adjusted upwards to achieve adequate plasma levels, and more time may be required to achieve satisfactory plasma levels.

For psychiatric patients, some have received two or more psychopharmaceuticals, and in some cases, two or more of the above examples describe different evaluations for the same period of administration of a psychopharmaceutical agent.

Of the patients who have received prescriptions for one or more of the medications as described in the examples above, each had previously demonstrated a significant intolerance to oral administration of one or more medications, prior to instituting transdermal administration. The laboratory measures of plasma blood levels described above for transdermally administered fluoxetine and carbamazepine are believed to demonstrate good absorption transdermally using lecithin organogel matrix as the vehicle. Valproic acid and sertraline do not appear to be absorbed well or reliably. Valproic acid appears to cause skin irritation in some patients necessitating discontinuation. Both the laboratory measure of Buproprion and the patient clinical responses indicated poor or equivocal absorptions and results. Patient tolerance of transdermal administration has been good to excellent. Patients in the example above who suffered very severe GI side effects using oral preparations were more tolerant of the inconvenience of rubbing on the gel than were patients who had experienced only mild to moderate side effects. In general, more highly motivated and treatment-compliant patients also had a higher rate of sustained compliance.

Patients in the examples above were evaluated by means of a structured evaluation form depicted in FIG. 1, which was completed at a frequency of at least one time per week for each patient receiving transdermal medication according to the present invention. The patients were evaluated both for all present psychiatric symptoms as well as any side effects from currently-administered medications. In general, it is believed that patients with the most clear cut and uncomplicated diagnosis of major depression experienced the best results. In general, patients with severe personality disorders or with concealed substance abuse disorders did less well.

Example 38

1800 mg of gabapentin in powder form is dissolved with 1 mL propylene glycol in syringes with a Luer Loc. 6.6 mL of Soya lecithin is added and mixed thoroughly between syringes. The resulting material is placed in a device for dispensing measured amounts.

Example 39

Gabapentin mixtures of 2% and 4% will be prepared by substituting 1200 mg gabapentin or 600 mg gabapentin in place of 1800 mg gabapentin, in example 38.

Example 40

Gabapentin, prepared according to Example 38 or 39, will be combined with either 3% or 5% Lidocaine in varying ratios.

Example 41

4% gabapentin, prepared according to Example 38 or 39, will be combined with 7% carbamazepine and 7% amitriptyline.

Example 42

2% gabapentin, prepared according to Example 38 or 39, will be combined with 2% carbamazepine and 1% Piroxicam, which is expected to yield better penetration into muscle tissue.

Example 43

Gabapentin, prepared according to Example 38 or 39, in concentrations ranging from 2%–6% will be combined with clonidine in concentrations between 0.2% and 0.3%.

Example 44

A 56-year-old woman had pill upper and lower extremity spasms as a result of spastic quadriparesis resulting from an injury. Oral gabapentin, an anticonvulsant, had been administered previously, but had caused a "drugged" feeling, one of the commonly reported side effects with this agent It was believed that use of transdermal gabapentin might provide local relief by achieving high local tissue concentrations near the site of administration without correspondingly elevated blood plasma levels. It is known that other anticonvulsants, such as carbamazepine, are useful in reducing neurogenic pain. Gabapentin's solubility in water exceeds 10%, making systemic absorption less likely. Gabapentin prepared according to the procedure of example 38 was self-administered by application to the skin in the area of pain. The patient reported moderate relief of spasms over a period of one week, with no systemic side effects and no report of skin irritation.

Example 45

Six grams of amitriptyline powder was placed in 40 milliliters of Pluronic F127 33% gel and placed under refrigeration to dissolve. Two milliliters of ethoxy diglycol was added to 4.8 grams of carbamazepine and mixed to form a smooth paste. 16.4 grams of soya lecithin was added to the resulting paste and mixed well. The dissolved amitriptyline composition was added to the carbamazepine composition and sufficient Pluronic F127 20% was added to make 120 milliliters and the resulting composition was mixed well to yield a composition having 5% amitriptyline and 4% carbamazepine.

Example 46

6 grams of doxepin was added to 20 milliliters Pluronic 33% F127 and put into a refrigerator to dissolve. 24 grams of ketoprofen and 12 grams of guaifenesin was added to 10 milliliters of 95% alcohol and mixed well. 26.4 milliliters of soya lecithin was added and mixed well and the doxepin composition was mixed well with the ketoprofen/ guaifenesin composition. The resulting mixture was added to sufficient Pluronic 33% to yield 120 milliliters. The resulting composition was mixed well to yield a composition having about 20% ketoprofen, 5% doxepin and 10% guaifenesin

Example 47

6 grams of doxepin was added to 26 milliliters Pluronic 33% and refrigerated to dissolve. 2 milliliters ethoxy diglycol was added 4.8 grams carbamazepine and mixed. The resultant mixture was added to 24 grams ketoprofen and six milliliters alcohol and the result was mixed well. 26.4 milliliters soya lecithin was added to the ketoprofen composition and mixed well. The doxepin composition was mixed with the carbamazepine/ketoprofen composition and sufficient Pluronic 33% was added to yield 120 milliliters. The resultant composition was mixed well to yield a composition having about 20% ketoprofen, 4% carbamazepine and 5% doxepin.

Example 48

0.15 grams sildenafil was crushed and strained and dissolved in 5 milliliters Pluronic 20% F127 and mixed between syringes. 2.2 milliliters of soya lecithin was added and mixed. Sufficient Pluronic 20% was added to yield 10 milliliters and the resultant composition was mixed well to yield a composition having the strength of about 15 milligrams per milliliter.

Example 49

A mixture of Sildenafil 15 mg/ml was applied to the penis and scrotum of a 51 year old male. An immediate and strong erection resulted with sexual stimulation, without any irritation or burning. It is believed the composition will possess the therapeutic results claimed for orally administered Sildenafil, without any time delay, without any systemic GI side effects, and possibly without the degree of drug interaction with nitrates used in cardiac disease. It is believed that this will contribute both to the convenience of use of the pharmaceutical and to its safety.

Example 50

Compositions according the examples 45 through 47, 53, 55 were transdermally applied to numerous patients, for the purpose of treating pain including as described in other examples herein, with the results summarized in Table I below. The meaning of certain entries in Table I is indicated in Table II below. Blank results indicate no treatment at the pertinent site for this patient. Where a given line of Table I shows more than one site, one "best" (greatest pain relief) result if shown in bold.

TABLE I

| Patient | Age | Gender | Surgery | Pain | Ketoprofen | Gabapentin | Piroxicam | doxepin | carbamazepine | amitriptyline | guifenesin | Duration | shoulder | back | neck | elbow | Knee | Wrist | Arm | Ankle | Hip | Leg |
|---|---|---|---|---|---|---|---|---|---|---|---|---|---|---|---|---|---|---|---|---|---|---|
| A | 50 | 2 | 2 | 3 | 10 | 3 | 4 | | | | | 2 | | 0 | | | | | | | | |
| B | 61 | 1 | 1 | 3 | | | | | | | | 4 | 2.0 | 2.0 | 2.0 | | | | | | | |
| B | 61 | 1 | 1 | 3 | 10 | 4 | 3 | 5 | 4 | | | 12 | | | | | | | 3.0 | | | |
| B | 61 | 1 | 1 | 3 | | 4 | | | | | | 6 | | 1.0 | | | | | | | | |
| C | 41 | 2 | 1 | 2 | | 4 | 1 | | 4 | 5 | | 2 | | | .0 | | | | | | | |
| D | 53 | 1 | 1 | 1 | 10 | 4 | | 5 | | | 1 | 1 | 1.0 | 2.0 | | | 1.5 | 1.0 | | | | |
| E | 57 | 2 | 2 | 3 | 10 | 4 | 3 | 10 | | | | 2 | 2.0 | 2.0 | | | | | | | | |
| E | 57 | 2 | 2 | 3 | 10 | 4 | | | 4 | | 5 | 8 | 2.0 | | | 3.0 | | | | | | |
| F | 38 | 2 | 2 | 3 | | 4 | | 5 | 4 | | | 4 | 2.0 | | | | | | 1.5 | | | |
| F | 38 | 2 | 2 | 2 | | 4 | 1 | | 4 | | | 6 | | | | | | | 1.0 | | | 1.0 |
| G | 39 | 1 | 1 | 2 | | | | | | | | 4 | | 2.0 | | 3.0 | | | | | | |
| H | 61 | 1 | 1 | 3 | 10 | | 3 | 5 | 5 | | 10 | 12 | 1.5 | | | | | | | | | |
| I | 49 | 1 | 1 | 3 | 10 | | 3 | | 4 | | | 1 | | | | | | | | | | |
| I | 49 | 1 | 1 | 3 | | | 4 | | 5 | | | 2 | | | | | | 2.0 | | | | |
| J | 54 | 1 | 1 | 3 | | | | | | 5 | | 2 | | | | | 2.0 | 1.0 | | | | |
| K | 40 | 2 | 2 | 3 | | | 3 | 5 | | | | 6 | 4.0 | 1.5 | | | | 3.0 | | | | |
| K | 40 | 2 | 2 | 3 | 10 | | 3 | 6 | | | | 4 | 1.0 | 3.0 | | | | | | | | |
| L | 55 | 1 | 1 | 2 | 10 | 4 | | 5 | | | | 8 | 1.0 | | | | | | | 1.5 | | |
| L | 55 | 2 | 2 | 2 | | | 4 | 4 | | | | 6 | | | | | | | .0 | .0 | | |
| M | 38 | 1 | 1 | 1 | 20 | 2 | 1 | 5 | 5 | 5 | | 2 | 1.5 | 3.0 | | | | .0 | | | | |
| N | 47 | 2 | 2 | 2 | 10 | 4 | | 6 | | | | 3 | 3.0 | 3.0 | 4.0 | | 1.0 | 2.0 | | | | |
| N | 47 | 2 | 2 | 2 | 20 | 4 | 3 | | | | | 2.0 | 2.0 | | 2.0 | | | | | | | |
| O | 57 | 1 | 1 | 2 | 20 | 4 | | 5 | | | | 24 | 2.0 | | 3.0 | 2.0 | | | | | | |
| O | 57 | 1 | 1 | 3 | 10 | 5 | 3 | 5 | | | | 24 | 1.0 | | | | | | | | | |
| P | 51 | 2 | 2 | 2 | 15 | | | 5 | | | | 2 | | .0 | | | | | | | | |
| Q | 51 | 2 | 2 | 2 | 20 | 4 | 1 | 5 | 4 | 5 | 10 | 1 | | 4.0 | | | | | | | | |
| R | 35 | 1 | 1 | 2 | 10 | 4 | 1 | | | | | 0 | | 2.0 | 3.0 | | | | | | | |
| R | 35 | 2 | 1 | 2 | 10 | 4 | 1 | | | | | 1 | | | | | 1.5 | | | | | |
| S | 55 | 1 | 1 | 2 | 10 | 4 | 1 | | | | | 16 | | 1.0 | | | 2.0 | | | | | |
| T | 50 | 2 | 2 | 2 | 10 | 4 | 1 | | | | | 16 | | .0 | | | | | | 2.0 | | |
| U | 45 | 2 | 2 | 3 | 10 | 4 | 3 | | | 6 | | 2 | | | | | 3.0 | | | | | |
| V | 57 | 2 | 2 | 3 | | 4 | | | | | | 8 | | | | | 1.0 | | | | | |
| V | 57 | 1 | 1 | 1 | 10 | 4 | 1 | 5 | 4 | | | 3 | 2.0 | 1.0 | 2.0 | 2.0 | | | | | | |
| W | 35 | 1 | 1 | 3 | 10 | 4 | 1 | 5 | | | | 8 | | 1.0 | | 1.5 | | | | | | |
| X | 46 | 1 | 1 | 3 | | 4 | | | | | | 8 | | 2.0 | | | | | | | | |
| Y | 48 | 2 | 2 | 3 | 10 | 4 | 1 | | | | | 4 | | 1.0 | | 1.5 | | 1.5 | | | .0 | |
| Y | 48 | 2 | 1 | 3 | | 4 | | | | Hand | | 4 | | 2.0 | | | | | | | | |
| AA | 53 | 1 | 1 | 1 | 10 | 4 | 1 | | | | 1 | 4 | | 1.0 | | | | | | | | |
| BB | 58 | 2 | 2 | 3 | 20 | 4 | | | 4 | | | 8 | | 2.0 | | | | | | | 2.0 | |

Result (Best result in Bold)

Medication Wt % in lecithin organogel

TABLE I-continued

| | | | | | | Medication Wt % in lecithin organogel | | | | | | | Result (Best result in Bold) | | | | | | | | | |
|---|---|---|---|---|---|---|---|---|---|---|---|---|---|---|---|---|---|---|---|---|---|---|
| Patient | Age | Gender | Surgery | Pain | Keto-profen | Gabapentin | Piroxicam | doxepin | carbamazepine | amitriptyline | guifenesin | Duration | shoulder | back | neck | elbow | Knee | Wrist | Arm | Ankle | Hip | Leg |
| CC | 59 | 1 | 1 | 2 | 10 | 4 | 1 | 5 | | | | 2 | | | 2.0 | | 2.0 | | | 2.0 | | |
| CC | 59 | 1 | 1 | 2 | 10 | 4 | 5 | | | | | 20 | | 1.0 | 2.0 | | 3.0 | 2.0 | | 3.0 | | |
| CC | 59 | 1 | 1 | 2 | 10 | 4 | 3 | | | | | 1 | | | | | 3.0 | | | | | |
| DD | 58 | 1 | 1 | 2 | 10 | 4 | 3 | | | | | 12 | | | 1.0 | | | 2.0 | | | | |
| EE | 45 | 2 | 2 | 2 | 10 | 4 | 3 | | | | | 24 | 1.5 | | 1.0 | | | | | | | |
| FF | 44 | 2 | 1 | 3 | 20 | 4 | 3 | | | | | 20 | 2.0 | | | | | | | | | |
| GG | 35 | 1 | 1 | 3 | | | | | | | | 4 | | | | 1.0 | 1.0 | | | | | |
| GG | 35 | 1 | 1 | 3 | | | | 5 | | | | 2 | | | | 1.0 | 1.0 | | | | | |
| GG | 35 | 1 | 1 | 3 | 20 | | | | 5 | 5 | | 2 | | | | | | .0 | | | | |
| GG | 35 | 1 | 1 | 3 | 20 | | | 5 | 5 | | | 2 | | | | | | 2.0 | | | | |
| GG | 35 | 1 | 1 | 3 | | 5 | | 5 | | | 10 | 4 | | | | | | 2.5 | | | | |
| HH | 40 | 1 | 2 | 2 | 10 | 4 | 3 | | | | | 8 | | 1.0 | | | 1.0 | | | | | |
| II | 40 | 1 | 1 | 3 | | | | 5 | | | | 8 | | 1.5 | | | | | | | | 1.5 |
| II | 40 | 1 | 2 | 2 | 10 | 4 | 3 | 5 | | | | 8 | | 2.0 | | | | | | | | |
| JJ | 45 | 1 | 1 | 3 | 10 | 4 | 3 | | | | | 2 | | 1.0 | | | | | | | | |
| KK | 37 | 2 | 2 | 2 | 10 | 4 | 1 | | | | | 8 | | 1.0 | | | | | | | | |
| LL | 54 | 1 | 1 | 3 | 10 | 4 | 3 | | | | | 6 | | | | | 1.0 | | | | | |
| LL | 54 | 1 | 1 | 3 | | | | | 4 | 5 | | 2 | | | | | .0 | | | | | |
| MM | 42 | 2 | 2 | 3 | | | | | 4 | | | 8 | | .0 | 4.0 | | | | 2.0 | | | 1.0 |
| MM | 42 | 2 | 1 | 3 | 10 | | 3 | | 4 | | | 12 | | .0 | | | | | | | | |
| MM | 42 | 2 | 1 | 3 | | | | 5 | | | | 4 | | | | | | 2.0 | | | | 1.0 |
| NN | 41 | 1 | 2 | 2 | 10 | 4 | 3 | | | | | 2 | | .0 | | | | | | | | |

TABLE II

Gender: 1 = male  2 = female
Surgery: 1 = one or more surgeries  2 = no surgeries
Pain: 1 = mild  2 = moderate  3 = severe-sufficient to produce observed tears
Duration: length of treatment trial in weeks
Result:  0 = no benefit
  1 = mild benefit
  2 = moderate benefit (greater than 25% pain reduction)
  3 = major benefit (greater than 40–45% pain reduction)
  4 = almost complete relief (greater than 80% pain reduction)

Certain results drawn from the information of Table I are summarized in Table III and IV.

TABLE III

Percent reported pain relief

| Site | N (Number of data points) | None | Mild | Mild-moderate | moderate | Major | Total |
|---|---|---|---|---|---|---|---|
| Wrist | 13 | 16.7 | 33.3 | 8.3 | 41.7 | | |
| Shoulder | 14 | 7.1 | 21.4 | 14.3 | 42.9 | 7.1 | 7.1 |
| Elbow | 5 | | 40 | 20 | 20 | 20 | |
| Back | 25 | 24 | 32 | 8 | 28 | 8 | |
| Arm | 7 | 28.6 | 14.3 | 14.3 | 28.6 | 14.3 | |
| Neck | 11 | 9.1 | 18.2 | | 45.5 | 9.1 | 18.2 |
| Knee | 13 | 15.4 | 46.2 | 15.4 | 7.7 | 15.4 | |

TABLE IV (percent reported pain relief)

| | N | None | Mild | Mild-moderate | moderate | Major | Total |
|---|---|---|---|---|---|---|---|
| Best result without tricyclic | 36 | 16.7 | 36.1 | 8.3 | 27.8 | 8.3 | 2.8 |
| Best result with any tricyclic | 20 | 10 | 10 | 20 | 35 | 15 | 10 |
| Either tricyclic -sole agent | 7 | | 14.3 | 14.3 | 42.9 | 14.3 | 14.3 |
| Best result with ketoprofen gabapentin piroxicam | 25 | 16 | 44 | 4 | 28 | 8 | |
| Best result without doxepin | 43 | 18.6 | 32.6 | 14 | 23.3 | 7 | 4.7 |
| Best result with doxepin | 13 | | 7.7 | 7.7 | 53.8 | 23.1 | 7.7 |

Example 51

A 51 year old female administered a composition prepared according to example 46, containing 20% ketoprofen, 5% doxepin, and 10% guaifenesin to her back for a period of 2 weeks. She reported moderate pain relief, lasting several hours, after each application. She reported no skin irritation nor any other side effects. Oral medications had produced no relief, and had caused significant GI side effects.

Example 52

A 34 year old man administered a composition containing 20% ketoprofen, 4% carbamazepine, and 5% doxepin to a very severely scarred wrist that had undergone 4 surgeries for carpel tunnel syndrome. He reported moderate pain relief, lasting for several hours after each application. No other treatment, including opiate oral pain medication, had been effective in providing even minor pain relief.

Example 53

24 grams ketoprofen and sufficient guaifenesin to result in a 10% final guaifenesin concentration, was mixed well with 10 milliliters 95% alcohol. 1200 mg gabapentin was dissolved in one ml propylene glycol in a syringe with a luer loc. 26.4 ml of soya lecithin was added to the ketoprofen-guaifenesin-alcohol mixture and mixed well. The resulting mixture was added to the gabapentin-propylene glycol mixture and mixed well. 4.8 gm of carbamazepine was combined with the resultant combination and mixed well to form a smooth paste. The resulting paste was combined with the ketoprofen-guaifenesin-alcoholgabapentin mixture and mixed well with sufficient pluronic to yield 120 ml of a composition containing ketoprofen 20%, carbamazepine 4%, gabapentin 4%, guaifenesin 10%.

Example 54

A 58 year old female with damage to her cervical spinal cord with a resultant spastic quadreparesis reported moderate relief of both pain and muscle spasms when she applied a mixture prepared generally according to example 53, containing ketoprofen 20%, carbamazepine 4%, gabapentin 4%, guaifenesin 10% for a period of 8 weeks to her back and hip. She had been unable to tolerate both oral carbamazepine and oral gabapentin because of systemic side effects, including skin rash with the carbamazepine and dizziness and sedation with the gabapentin. She experienced no skin irritation nor other side effects with the transdermal formulation.

Example 55

Six grams of doxepin powder combined with 26 milliliters pluronic and placed in the refrigerator until dissolved. 1200 mg gabapentin was mixed with 1 ml propylene glycol and placed in a syringe with luer lock. 6.6 ml of soya lecithin was added and mixed well between syringes. 24 gm of ketoprofen and 8 milliliters alcohol was mixed well between two syringes with luer loc. The doxepin mixture was mixed well with the gabapentin mixture and subsequently the ketoprofen mixture was added and mixed well. Sufficient pluronic 20% (about 54 ml) was added to yield 60 ml of a composition having about 20% ketoprofen, 4% weight percent gabapentin and 5% weight percent doxepin.

Example 56

A 57 year old female applied a mixture, prepared generally according to example 55, containing ketoprofen 20%, gabapentin 4%, and doxepin 5% for a period of 8 weeks to her neck and reported major relief. She applied the same mixture to her shoulder and reported moderate relief. A mixture that substituted piroxicam for the doxepin produced only mild shoulder relief.

Example 57

A 35 year old man with a history of knee injury with vascular compromise and 3 surgeries applied a mixture, prepared generally according to example 45, containing 4% carbamazepine and 5% amitriptyline to his knee, and reported mild to moderate pain relief, without skin irritation nor other side effects.

Example 57A

A 41 year old woman with history of back surgery applied a mixture, prepared generally according to example 45, containing 4% carbamazepine and 5% gabapentin to her back for a period of 2 weeks. She reported mild pain relief.

Example 58

A 53 year old man with a history of two total bilateral knee replacements applied a mixture, prepared generally according to example 45, containing 4% carbamazepine and 5% amitriptyline to both knees for a period of 4 weeks. He reported no pain relief.

Example 58A

A 54 year old man with a history of 7 back surgeries applied a mixture, prepared generally according to example 45, containing 4% carbamazepine and 5% amitriptyline to his back for a period of 2 weeks. He reported mild to moderate pain relief, over and above that he was receiving from a transdermal opiate medication (Duragesic). He reported no side effects, and specifically no skin irritation.

Example 59

A 38 year old man with a history of shoulder strain applied a mixture, prepared generally according to example 45, containing 4% carbamazepine and 5% amitriptyline to his shoulder for a period of 2 weeks. He reported mild to moderate pain relief, and reported no skin irritation nor other side effects.

Example 61

Sufficient carbamazepine and gabapentin was added to a combination of soya lecithin and pluronic to yield a lecithin organogel out 4%/a carbamazeprine 5% gabapentin.

Example 62

A 42 year old woman with a history of 3 back surgeries and cervical degenerative disc disease applied a mixture, prepared according to example 61, containing 4% carbamazepine and 5% gabapentin to her neck and reported total relief of pain. She reported no side effects, and no skin irritation. She noted the complete and rapid resolution of a migraine like headache at the same time. Administration of the same mixture to her arm and her wrist, affected by a diagnosed condition of reflex sympathetic dystrophy, yielded moderate pain relief.

Example 63

3.6 grams gabapentin was dissolved with 5.4 ml ethoxy diglycol using a mortar and pestle. 9.6 grams ketoprofen and 2.7 grams piroxicam were added and the resultant composition mixed well. 19.8 milliliters soya lecithin was added and resultant mixture mixed well and added to a sufficient quantity of 20% pluronic gel to yield 90 milliliters of a composition having about 10 percent ketoprofen, 4% gabapentin and 3% piroxicam.

Example 64

3.6 grams gabapentin was dissolved with 5.4 ml ethoxy diglycol using a mortar and pestle. 9 grams ketoprofen and 0.9 grams piroxicam were added and mixed well. 19.8 milliliters soya lecithin was added to the resultant mixture and mixed well. Sufficient amount of pluronic gel 20% was added to yield 90 milliliters of a composition having approximately 10% ketoprofen, 4% gabapentin and 1% prioxicam.

Example 65

12 g doxepin was mixed with 50 ml Pluronic F 127 33% and placed in a refrigerator to dissolve. 12 g gabapentin was dissolved in 9 ml ethoxy diglycol and mixed to form a smooth paste. 52.8 ml of soya lecithin was added and mixed well. The doxepin/Pluronic mixture was added and mixed well. Sufficient quantity of Pluronic F 127 20% was added to produce 240 ml of a composition having about 5 wt % gabapentin and 5 wt % doxepin.

Example 66

A 36 year old man with a knee injury involving joint surface damage and vascular comprise applied a mixture, prepared generally according to Example 65 to his knee several times per day. He reported moderate to major (40%) relief of pain that persisted for 4 to 6 hours. An earlier trial of carbamazepine-amitriptyline gel produced no relief when applied to his knee.

Example 67

6 gm doxepin was mixed with 18 ml of Pluronic 33% to and placed in a refrigerator to dissolve. 6 gm gabapentin was ground in a mortar and pestle to a fine powder, added to 6 ml ethoxy diglycol and mixed to form a smooth paste. 12 gm guaifenesin was added and mixed well. 26.4 ml soya lecithin was added and mixed well. The doxepin/Pluronic mixture was added and mixed well. Sufficient quantity of Pluronic gel (25.2 ml of 33% Pluronic, although 30% or 20% Pluronic can be used), was added to produce 120 ml of a composition having about 5 wt % gabapentin, about 5 wt % doxepin and about 10 wt % guaifenesin.

Example 68

A 55 year old woman with a back and shoulder injury sustained as a nursing care provider applied a mixture, prepared generally according to Example 67, to her back three times per day for a period of two weeks and achieved major relief She applied the same mixture to her hip and leg and reported moderate to major relief A mixture containing only doxepin provided only moderate relief to her back, and mild to moderate relief to her hip and leg. A mixture that contained only ketoprofen, gabapentin and piroxicam provided only mild relief to her back.

Example 69

A 59 year old woman with cervical and back strain applied a mixture, prepared generally according to example 51, but without steps involving ketoprofen) containing about 5 wt % doxepin and about 10 wt % guaifenesin, to her neck for a period of two weeks, two to four times per day, and achieved total relief. She applied the same mixture to her back and achieved major to total relief.

Example 70

4.5 gm of doxepin HCl was dissolved using 2.5 ml 95% alcohol and mixed well between syringes. It is also possible to mix the doxepin with 5 ml Pluronic 20% and place in a refrigerator to dissolve. Sufficient quantity of 20% Pluronic F127 was added to produce 90 ml of a composition having about 5 wt % doxepin. Preferably this and other disclosed compositions are protected from light.

Example 71

A 61 year old man with injuries to his back, neck and arm applied a mixture (prepared generally according to Example 70) to his neck four times per day and achieved major relief. He applied the same mixture to his elbow and achieved moderate relief.

Example 72

A formulation of 7% antidepressant and about 10% muscle relaxant was prepared by dissolving 3.15 g of trimipramine and 4.5 g of guaifenesin in a mixer jar using 2.7 mL of ethoxy diglycol. About 9.9 mL of soya lecithin was added and the mixture was mixed well. Sufficient quantity of Pluronic F127 NF (20%) to make total volume of about 45 mL was added and mixed well.

Example 73

A gel formulation of 30% NTHE was prepared from 36 g of celecoxib, 7.2 mL of ethoxy diglycol, 26.4 mL of soya lecithin and sufficient quantity of Pluronic F127 NF (20%) to make total volume of 120 mL.

Example 74

A gel formulation containing about 7% antidepressant and about 13% muscle relaxant was prepared from 14.4 g of doxepin, 31.2 g of guaifenesin, 12 mL of ethoxy diglycol, 52.8 mL of soya lecithin and sufficient quantity of Pluronic F127 NF (33%) to make total volume of 240 mL.

Example 75

A gel formulation containing 5% antiepileptic was prepared from 6 g of lamotrigine, 6 mL of ethoxy diglycol, 26.4 mL of soya lecithin and sufficient quantity of Pluronic F127 NF (33%) to make total volume of 120 mL.

Example 76

A gel formulation containing 10% adrenergic agonist was prepared from 12 g of crushed tizanidine, 6 mL of ethoxy diglycol, 26.4 mL of soya lecithin and sufficient quantity of Pluronic F127 NF (33%) to make total volume of 120 mL.

Example 77

A gel formulation containing 10% muscle relaxant was prepared from 12 g of crushed metaxalone, 6 mL of ethoxy diglycol, 26.4 mL of soya lecithin and sufficient quantity of Pluronic F127 NF (33%) to make total volume of 120 mL.

Example 78

A gel formulation containing 10% muscle relaxant was prepared from 12 g of crushed carisoprodol, 6 mL of ethoxy diglycol, 26.4 mL of soya lecithin and sufficient quantity of Pluronic F 127 NF (33%) to make total volume of 120 mL.

Example 79

A gel formulation containing 10% methocarbamol was prepared from 12 g of crushed methocarbamol, 6 mL of ethoxy diglycol, 26.4 mL of soya lecithin and sufficient quantity of Pluronic F127 NF (33%) to make total volume of 120 mL.

Example 80

A gel formulation containing 10% muscle relaxant was prepared from 12 g of crushed dantrolene sodium, 6 mL of ethoxy diglycol, 26.4 mL of soya lecithin and sufficient quantity of Pluronic F127 NF (33%) to make total volume of 120 mL.

Example 81A

A gel formulation containing 7% antidepressant, 10% muscle relaxant was prepared from 8.4 g of crushed doxepin, 12 g of chlorzoxazone, 6 mL of ethoxy diglycol, 26.4 mL of soya lecithin and sufficient quantity of Pluronic F127 NF (33%) to make total volume of 120 mL.

Example 82

A series of experiments in human subjects were performed using various combinations of pharmaceuticals. The results are indicated in FIG. 2.

Values of pain relief as rated by the patients are provided for each body part for which the medication was administered. The scale used in FIG. 2, is as follows:

| | | |
|---|---|---|
| 0 = | None | no benefit or equivalent benefit |
| 1 = | Mild | less than 15% pain reduction |
| 1.5 = | Mild-moderate | 15–33% pain reduction |
| 2.0 = | Moderate | 25–25% pain reduction |
| 2.5 = | Moderate-major | 33–45% pain reduction |
| 3.0 = | Major | 45–60% pain reduction |
| 3.5 = | Major-total | 60–80% pain reduction |
| 4.0 = | Total | greater than 80% pain reduction |

For each body part and for each percentage composition of each compounded medication, the individual ratings as well as a mean, which is the statistical mean of the values given according to the scale listed above, are provided. For example, 3 patients were administered doxepin 5% to their back, and the mean level of relief was 2.333. By contrast, 13 patients received the 5%/10% doxepin-guaifenesin combination, and their mean level of pain relief was 2.885. Results for 7/10 and 10/10 compositions of doxepin guaifenesin are also given, and the mean for the entire sample of dox-guai in all combinations is provided at the end of the section, namely 2.722.

The abbreviations used in FIG. 2 are as follows:

| Abbreviations | Generic Pharmaceutical names |
|---|---|
| c-dox-gu | carbamazepine doxepin guaifenesin |
| c-gab-do | carbamazepine gabapentin doxepin |
| carb | carbamazepine |
| carb-ami | carbamazepine amitriptyline |
| carb-gab | carbamazepine gabapentin |
| dox | doxepin |
| dox-chl | doxepin chlorzoxazone |
| dox-guai | doxepin guaifenesin |
| g-dox-gu | gabapentin doxepin guaifenesin |
| gab-dox | gabapentin doxepin |
| k-ca-dox | ketoprofen carbamazepine doxepin |
| k-car-pi | ketoprofen carbamazepine piroxicam |
| k-dox-ch | ketoprofen doxepin chlorozoxazone |
| k-dox-gu | ketoprofen doxepin guaifenesin |
| k-dox-pi | ketoprofen doxepin piroxicam |
| k-g-do-g | ketoprofen gabapentin doxepin guaifenesin |
| k-gab | ketoprofen gabapentin |
| k-gab-ami | ketoprofen gabapentin amitriptyline |
| k-gab-do | ketoprofen gabapentin doxepin |
| k-gab-gu | ketoprofen gabapentin guaifenesin |
| k-gab-pi | ketoprofen gabapentin piroxicam |
| k-pi | ketoprofen piroxicam |
| la-li-gu | lamotrigine lidocaine guaifenesin |
| lam-chl | lamotrigine chlorzoxazone |
| n-dox-ch | naproxen doxepin chlorzoxazone |
| naproxen | naproxen |
| tri-chl | trimipramine chlorzoxazone |

Based on the results described herein, doxepin appears to be an effective pain relief medication when administered transdermally and appears to be substantially free of side effects when administered transdermally as described herein.

Doxepin appears to provide about three times the positive response rate compared to at least some other pharmaceutical agents described herein, regardless of whether such other pharmaceutical agents are administered singly or in combination. Doxepin appears to be substantially more effective than amitriptyline as a pain, e.g., neuropathic pain agent when administered transdermally. This appears to be true regardless of whether doxepin is administered as a single agent or is administered in combination with other pharmaceuticals as described herein.

Carbamazepine appears to provide positive effects as a pain, e.g., neuropathic pain agent, at least in properly selected patients. Carbamazepine appears to cause a rash in at least some patients, requiring its discontinuation.

These side effects appear similar to those that are noted for oral administration of carbamazepine. Gabapentin appears to be free of side effects when administered transdermally. Although some patients appear to derive some benefit from a combination of transdermally administered ketoprofen, gabapentin, and prioxicam, the effect appears to be relatively weak compared to the effect provided by doxepin.

Guaifenesin appears to provide benefit as an adjunctive treatment, of painful spasticity. For the patient population described herein, amitriptyline appeared to offer limited pain relief when administered transdermally. It appears that combining gabapentin with doxepin may offer some additional benefit. The addition of guaifenesin to doxepin may be of particular value when painful spasticity is present.

In view of the above, the invention provides treatment to patients for whom oral delivery is suboptimal, such as patients who experience gastrointestinal or other side effects, patients who experience poor absorption for orally delivered pharmaceuticals and/or patients who benefit from delivery over an extended period or a relatively rapid delivery or higher rate of increase of plasma levels. The present invention achieves delivery of therapeutic amounts of pharmaceuticals, for at least some patient populations, substantially without skin irritation, gastrointestinal or other side effects associated with orally-delivered pharmaceuticals, especially psychopharmaceuticals, and yields clinical benefits comparable to or greater than those received by patients to whom corresponding pharmaceuticals were administered orally. In view of the above reasons, particularly effective pain medications are those described in examples 65, 67, 69 and 70.

A number of variations and modifications of the invention can also be used. It is believed that blood plasma levels may be increased by providing for two or more transdermal applications per day and/or applying a transdermal composition to two or more sites.

In at least one case, application of a Prozac gel formulation twice daily appeared to approximately double the plasma level. It is believed that an approach such as applying a Prozac gel formulation twice daily to two sites will yield middle range therapeutic levels of about 140–250 ng/ml. At least partially on the basis of the results described herein for fluoxetine, it is believed olanzapine (sold under the trade name Zyprexa) or a fluoxetine/olanzapine mixture in a lecithin organogel will prove useful.

Other types of psychotropic or psychopharmaceutical medications for which the described transdermal delivery may be used including psychostimulant medications. One example of a psychostimulant medication is Methylphenidate (sold under the trade name Ritalin) used in the treatment of attention deficit hyperactivity disorder (ADHD). Methylphenidate typically has a 2–4 hour duration of action necessitating frequent dosing of a patient which is particularly difficult to accomplish with children in school. It is believed that by using transdermal administration, it will be possible to achieve an extension of effective dosing throughout the day, eliminating the need for frequent oral medication administration. It is believed that transdermal administration will also eliminate peaks and valleys of blood plasma levels which, it is believed, will be more clinically effective. It is believed similar results will be obtained with other pharmaceuticals, for example, Dextroamphetamine (under the trade name Dexedrine) although it is believed the need is less acute since a time release "spansule" form of the medication is available which typically has a 5–6 hour duration of action. Another group of psychotropic medications which, it is believed, will benefit from transdermal delivery includes antipsychotic medication such as those used in the treatment in schizophrenia.

Embodiments of the invention include, but are not necessarily limited to, use by patients with enteric absorption deficits.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating pain in a subject comprising contacting said subject with a transdermal composition comprising:

a psychopharmaceutical and guaifenesin in an amount effective to treat pain, and lecithin organogel, thereby treating pain in said subject.

2. The method of claim 1, wherein said psychopharmaceutical is selected from the group consisting of sertraline, fluoxetine, carbamazepine, amitriptyline, trazodone, fluvoxamine, pemoline, pergolide, bromocriptine mesylate, propranolol, buproprion, reboxetine, valproic acid, nefazodone and doxepin.

3. The method of claim 1, wherein said transdermal composition further comprises Pluronic F127.

4. The method of claim 1, wherein said psychopharmaceutical is doxepin.

5. The method of claim 1, wherein said transdermal composition comprises about 5 wt % doxepin.

6. The method of claim 1, wherein said transdermal composition comprises about 10 wt % guaifenesin.

7. The method of claim 1, wherein said transdermal composition comprises about 5 wt % doxepin and about 10 wt % guaifenesin.

8. A method for treating pain in a subject comprising contacting said subject with a transdermal composition comprising:
    doxepin and guaifenesin in an amount effective to treat pain, and lecithin organogel,
    thereby treating pain in said subject.

9. The method of claim 8, wherein said transdermal composition comprises about 5 wt % doxepin.

10. The method of claim 8, wherein said transdermal composition comprises about 10 wt % guaifenesin.

11. The method of claim 8, wherein said transdermal composition comprises about 5 wt % doxepin and about 10 wt % guaifenesin.

12. A method for treating pain in a subject comprising contacting said subject with a transdermal composition comprising:
    doxepin and guaifenesin in an amount effective to treat pain, Pluronic F127, and lecithin organogel,
    thereby treating pain in said subject.

13. The method of claim 12, wherein said transdermal composition comprises about 5 wt % guaifenesin.

14. The method of claim 12, wherein said transdermal composition comprises about 10 wt % guaifenesin.

15. The method of claim 12, wherein said transdermal composition comprises about 5 wt % doxepin and about 10 wt % guaifenesin.

16. A method for treating pain in a subject comprising contacting said subject with a transdermal composition comprising:
    about 5 wt % doxepin, about 10 wt % guaifenesin, and lecithin organogel,
    thereby treating pain in said subject.

17. A method for treating pain in a subject comprising contacting said subject with a transdermal composition comprising:
    about 5 wt % doxepin, about 10 wt % guaifenesin, Pluronic F127, and lecithin organogel,
    thereby treating pain in said subject.

* * * * *

UNITED STATES PATENT AND TRADEMARK OFFICE
CERTIFICATE OF CORRECTION

PATENT NO.    : 6,479,074 B2
DATED         : November 12, 2002
INVENTOR(S)   : Robert W. Murdock et al.

It is certified that error appears in the above-identified patent and that said Letters Patent is hereby corrected as shown below:

<u>Column 36,</u>
Line 8, delete the word "guaifenesin" and replace it with the word -- doxepin --

Signed and Sealed this

Thirteenth Day of May, 2003

JAMES E. ROGAN
*Director of the United States Patent and Trademark Office*